US012685644B2

(12) United States Patent
Ginn et al.

(10) Patent No.: US 12,685,644 B2
(45) Date of Patent: Jul. 21, 2026

(54) MULTI-FUNCTION BONE STRUCTURE PROSTHESES

(71) Applicant: Tenon Medical, Inc., Los Gatos, CA (US)

(72) Inventors: Richard S Ginn, Gilroy, CA (US); Richard Brown, Colorado Springs, CO (US)

(73) Assignee: Tenon Medical, Inc., Los Gatos, CA (US)

( * ) Notice: Subject to any disclaimer, the term of this patent is extended or adjusted under 35 U.S.C. 154(b) by 989 days.

(21) Appl. No.: 17/903,310

(22) Filed: Sep. 6, 2022

(65) Prior Publication Data

US 2023/0000631 A1 Jan. 5, 2023

Related U.S. Application Data

(63) Continuation-in-part of application No. 17/833,960, filed on Jun. 7, 2022, now Pat. No. 12,582,528, which
(Continued)

(51) Int. Cl.
*A61F 2/30* (2006.01)
*A61B 5/055* (2006.01)
(Continued)

(52) U.S. Cl.
CPC .......... *A61F 2/30988* (2013.01); *A61B 5/055* (2013.01); *A61B 5/062* (2013.01);
(Continued)

(58) Field of Classification Search
CPC .............. A61B 5/4893; A61B 17/7092; A61B 2017/00039; A61B 5/296; A61B 5/24; A61B 5/4041; A61F 2002/30166; A61F 2002/30123; A61F 2002/3013; A61F 2/30988; A61F 2002/30995; A61F 2002/30121
See application file for complete search history.

(56) References Cited

U.S. PATENT DOCUMENTS 6,499,488 B1 * 12/2002 Hunter ................... A61B 90/39
128/899
7,519,429 B2 4/2009 Sawan et al.
(Continued)

FOREIGN PATENT DOCUMENTS

WO WO-2022/125619 A1 6/2022

*Primary Examiner* — Lynnsy M Summitt
(74) *Attorney, Agent, or Firm* — Francis Law Group

(57) ABSTRACT

A system for treating dysfunctional SI joints that includes a multi-function bone structure prosthesis adapted to be delivered to and inserted into a dysfunctional SI joint via a posterior approach, the multi-function bone structure prosthesis, when disposed in a dysfunctional SI joint, being adapted to (i) stabilize the dysfunctional SI joint, (ii) induce proliferation, and/or growth and/or remodeling and/or regeneration of osseous tissue and, thereby, healing and arthrodesis of the dysfunctional SI joint, (iii) attenuate pain associated with the dysfunctional SI joint via neurostimulation, and (iv) monitor physiological and/or biomechanical parameters associated with the dysfunctional SI joint via one or more sensor systems.

13 Claims, 17 Drawing Sheets

Related U.S. Application Data is a continuation-in-part of application No. 17/833,098, filed on Jun. 6, 2022, now Pat. No. 12,551,348, which is a continuation of application No. 17/749,199, filed on May 20, 2022, now Pat. No. 12,465,491, which is a continuation-in-part of application No. 17/740,568, filed on May 10, 2022, now Pat. No. 12,472,069, which is a continuation-in-part of application No. 17/463,779, filed on Sep. 1, 2021, now Pat. No. 12,427,027, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | |
|---|---|
| *A61B 5/06* | (2006.01) |
| *A61B 6/00* | (2006.01) |
| *A61B 6/03* | (2006.01) |
| *A61B 8/08* | (2006.01) |
| *A61B 17/16* | (2006.01) |
| *A61B 17/70* | (2006.01) |
| *A61B 17/88* | (2006.01) |
| *A61B 34/20* | (2016.01) |
| *A61F 2/44* | (2006.01) |
| *A61F 2/46* | (2006.01) |

(52) U.S. Cl.
CPC .............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 7,582,058 | B1 * | 9/2009 | Miles ................. | A61B 17/0293 |
| | | | | 607/2 |
| 7,981,144 | B2 * | 7/2011 | Geist ...................... | A61B 5/296 |
| | | | | 606/76 |
| 8,348,983 | B2 * | 1/2013 | Neubardt ........... | A61B 17/8625 |
| | | | | 600/377 |
| 8,591,431 | B2 * | 11/2013 | Calancie ........... | A61N 1/37247 |
| | | | | 600/554 |
| 9,131,947 | B2 * | 9/2015 | Ferree ................ | A61B 17/1671 |
| 9,278,214 | B2 * | 3/2016 | Young .................. | A61B 5/4041 |
| 9,724,151 | B2 * | 8/2017 | Edidin .................. | A61B 18/04 |
| 9,737,233 | B2 * | 8/2017 | Londot .................. | A61B 5/053 |
| 9,844,662 | B2 * | 12/2017 | Leuthardt .............. | A61B 17/56 |
| 10,154,866 | B2 * | 12/2018 | Kim ...................... | A61B 5/296 |
| 10,172,658 | B2 * | 1/2019 | Kim ...................... | A61C 8/0039 |
| 10,179,014 | B1 * | 1/2019 | Menmuir ............. | A61B 17/864 |
| 10,278,737 | B2 * | 5/2019 | Smith ................ | A61B 17/7032 |
| 10,376,367 | B2 * | 8/2019 | Fallin ................. | A61B 17/8004 |
| 10,646,258 | B2 | 5/2020 | Donner et al. | |
| 10,675,458 | B2 * | 6/2020 | Molnar ............. | A61B 17/7043 |
| 10,933,234 | B2 * | 3/2021 | Molnar ............... | A61N 1/0558 |
| 11,109,899 | B2 * | 9/2021 | Kim ...................... | A61B 5/0538 |
| 11,752,011 | B2 * | 9/2023 | Stuart .................... | A61F 2/447 |
| | | | | 623/17.11 |
| 2004/0102828 | A1 * | 5/2004 | Lowry ................. | A61N 1/0534 |
| | | | | 607/116 |
| 2004/0243207 | A1 * | 12/2004 | Olson ...................... | A61N 1/05 |
| | | | | 607/116 |
| 2006/0200023 | A1 * | 9/2006 | Melkent ............... | A61B 5/4041 |
| | | | | 600/373 |
| 2009/0054951 | A1 * | 2/2009 | Leuthardt .......... | A61B 17/8625 |
| | | | | 607/51 |
| 2010/0106198 | A1 * | 4/2010 | Adcox ................ | A61N 1/3605 |
| | | | | 606/301 |
| 2012/0185001 | A1 * | 7/2012 | Nayet ................ | A61B 17/8875 |
| | | | | 606/301 |
| 2012/0296428 | A1 | 11/2012 | Donner | |
| 2014/0142700 | A1 * | 5/2014 | Donner .............. | A61B 17/1739 |
| | | | | 623/17.11 |
| 2014/0200668 | A1 * | 7/2014 | Kirschman .......... | A61B 17/025 |
| | | | | 623/17.16 |
| 2021/0268294 | A1 | 9/2021 | Maharbiz et al. | |
| 2021/0401581 | A1 | 12/2021 | Ginn et al. | |

* cited by examiner

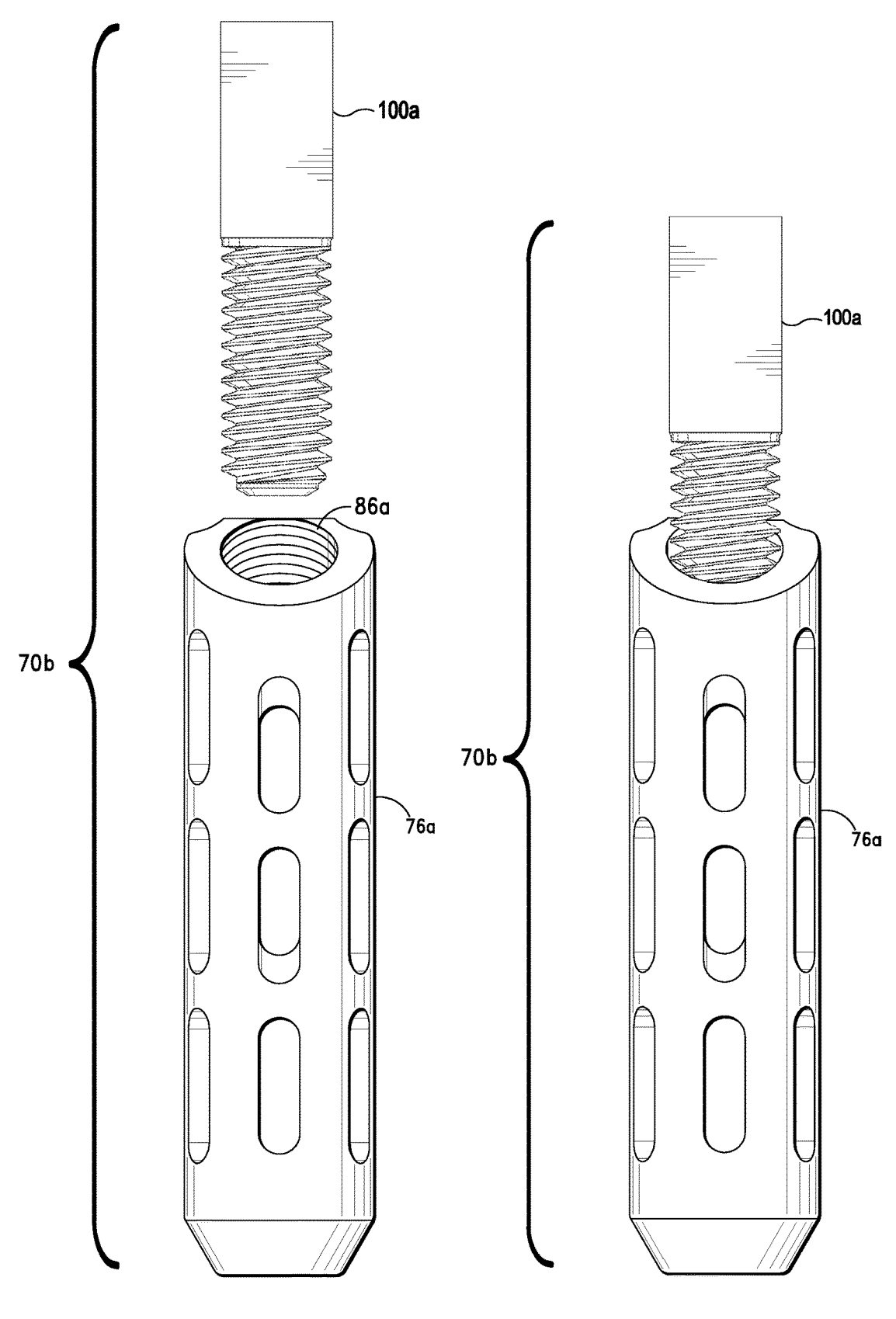
*FIG. 5*          *FIG. 6*

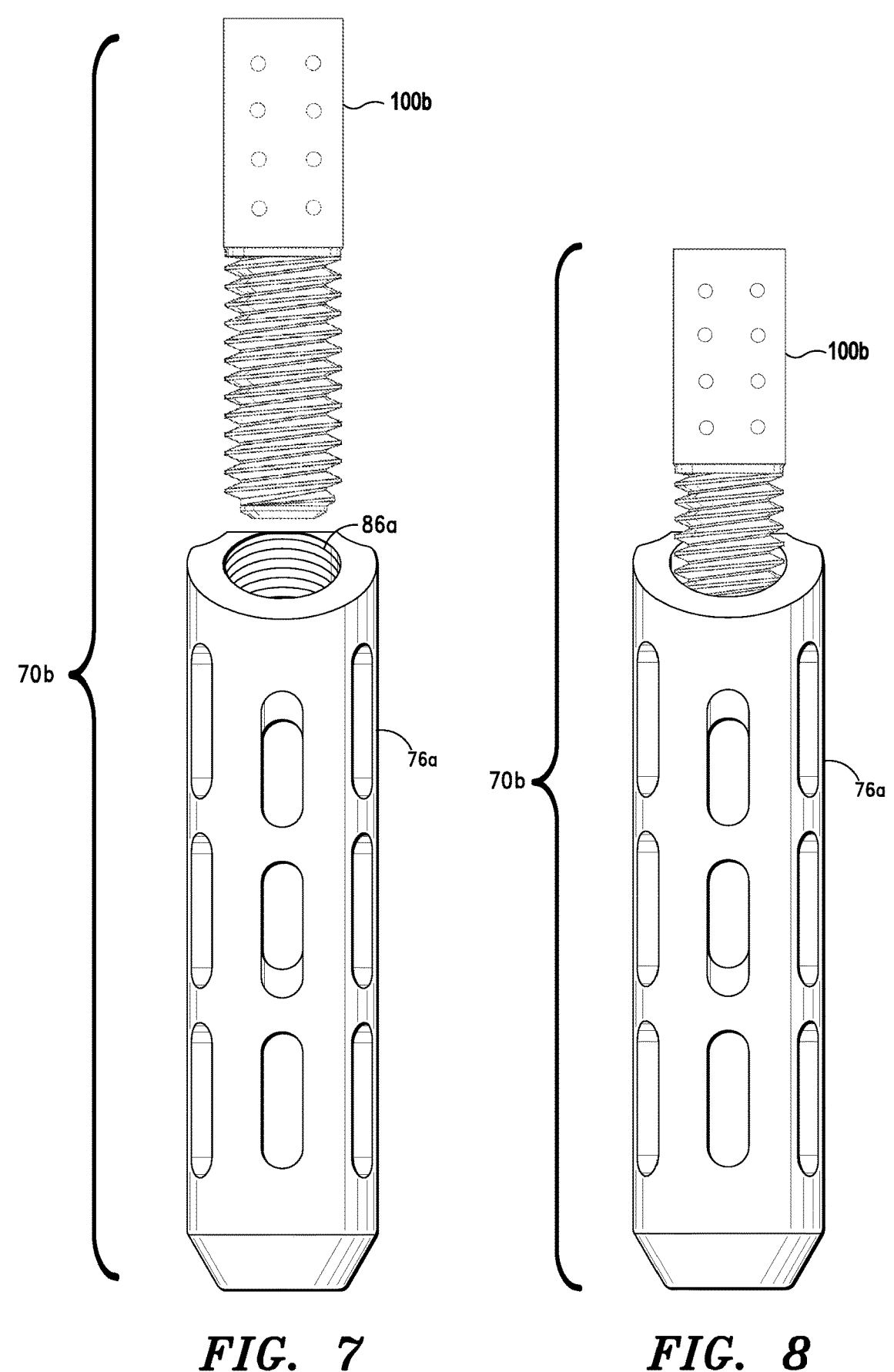
*FIG. 7*    *FIG. 8*

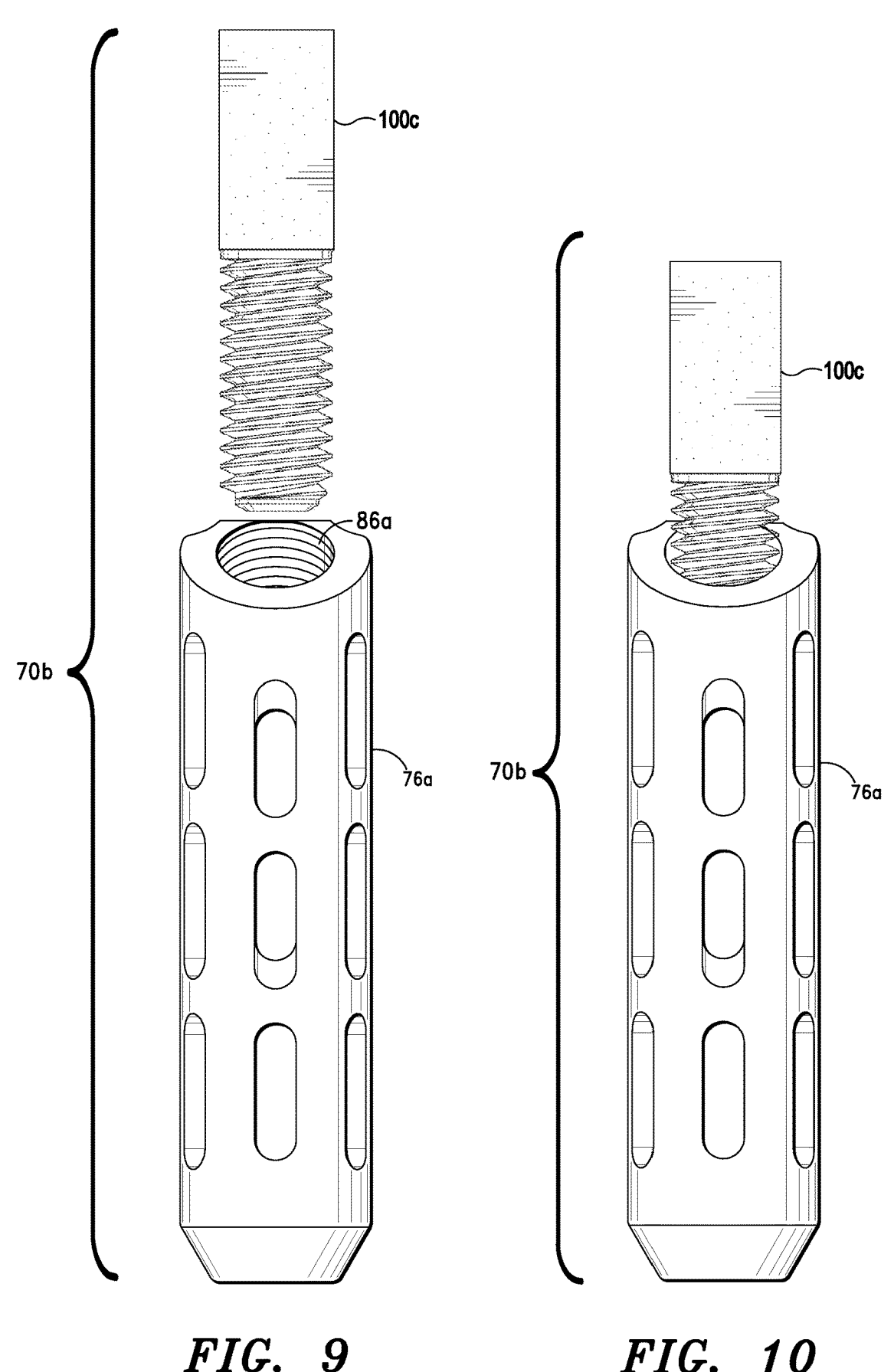
FIG. 9          FIG. 10

MULTI-FUNCTION BONE STRUCTURE PROSTHESES

CROSS-REFERENCES TO RELATED APPLICATIONS

This application is a continuation-in-part of U.S. application Ser. No. 17/833,960, filed Jun. 7, 2022, which is a continuation-in-part of U.S. application Ser. No. 17/833,098, filed Jun. 6, 2022, which is a continuation of U.S. patent application Ser. No. 17/749,199, filed on May 20, 2022, which is a continuation-in-part application of U.S. patent application Ser. No. 17/740,568, filed on May 10, 2022, which is a continuation-in-part application of U.S. patent application Ser. No. 17/463,779, filed Sep. 1, 2021, which is a continuation-in part of U.S. patent application Ser. No. 13/857,977, filed Apr. 5, 2013, now U.S. Pat. No. 11,273,042, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to systems, apparatus and methods for treating dysfunctional bone structures. More particularly, the present invention relates to systems, apparatus and methods for treating dysfunctional sacroiliac (SI) joints and structures proximate thereto.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As further illustrated in FIGS. 1B-1D, the SI joint 6 generally comprises the shape of an inverted capital letter "L" (denoted "13") lying on its side (rather than a triangle), where the long arm of the inverted "L" 15 (i.e., SI joint 6) is oriented along the posterior wall of the pelvis 11 (denoted "25" in FIG. 1A) and is also oriented relatively straight through its entire course. The sacral floor (denoted "21" in FIG. 1C), which is defined by the region between the anterior sacral promontory 19*a* and the apex 19*b* of the sacrum 2, generally slopes downward and laterally at an approximately 30% grade relative to the cephalocaudal axis 27.

As illustrated in FIGS. 1B and 1C, the short arm of the inverted "L" (denoted "17") is generally oriented parallel to the transverse plane of the L5-S1 lumbosacral joint and limited superiorly by the sacral ala (denoted "23" in FIG. 1C).

The apex of the inverted "L" (denoted "29" in FIG. 1B) is positioned below the S2 segment region of the sacrum 2 (denoted "S2") proximate to the S3 segment region of the sacrum 2 (denoted "S3").

As is also well known in the art, the SI joint further comprises a SI joint dorsal recess or gap 7 that is disposed between the sacrum 2 and ilium 4 proximate the S2 segment region of the sacrum 2, as illustrated in FIG. 1D.

As is further well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans illi, and other degenerative conditions of the SI joint structures and associated structures.

Various non-surgical methods, such as administration of pharmacological agents, e.g., the corticosteroid prednisone, and surgical methods and devices, i.e., SI joint prostheses, have been developed and employed to treat SI joint dysfunction and the pain associated therewith.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a bone structure prosthesis proximate to or in a dysfunctional SI joint and is generally characterized by the direction of access to the dysfunctional SI joint, i.e., anterior, posterior or lateral.

Although several conventional SI joint stabilization surgical methods and associated bone structure prostheses have effectively ameliorated pain associated with SI joint dysfunction, there remains many disadvantages associated with the conventional surgical methods and associated bone structure prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive systems and methods for SI joint stabilization have thus been developed to address the noted disadvantages associated with open surgery methods. Although conventional minimally-invasive SI joint stabilization systems and methods, such as the systems and methods disclosed in U.S. Pub. No. 2009/0076551 to Petersen, have garnered some success in relieving pain associated with SI joint dysfunction and have effectively addressed many of the disadvantages associated with open surgery systems and methods, there similarly remains many disadvantages associated with conventional minimally-invasive SI joint stabilization systems and methods.

A major disadvantage associated with many conventional minimally-invasive SI joint stabilization methods is that such methods are difficult to perform and the associated surgical systems often require extensive, system-specific surgical training and experience. Indeed, it has been found that, notwithstanding the level of surgical training and experience that a surgeon may possess, when such conventional minimally-invasive SI joint stabilization systems and methods are employed, there is still a substantial incidence of damage to the lumbosacral neurovascular structures proximate to the SI joint.

A further disadvantage associated with many conventional minimally-invasive SI joint stabilization systems and methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a bone structure prosthesis in a dysfunctional SI joint.

Further, although some conventional minimally-invasive SI joint stabilization systems comprise a bone structure prosthesis that is adapted to deliver osteogenic material and/or compositions to a bone structure when implanted therein, such as the prostheses disclosed in Applicant's Co-pending U.S. application Ser. Nos. 17/469,132, 17/468,811, and 17/463,831, most, if not all, bone structure prostheses have limited functionality, e.g., not adapted to monitor physiological or biomechanical parameters associated with a bone structure.

It would thus be desirable to provide improved SI joint stabilization systems, apparatus and methods that substantially reduce or eliminate the disadvantages associated with conventional SI joint stabilization systems, apparatus and methods.

It is therefore an object of the invention to provide improved SI joint stabilization systems, apparatus and methods that substantially reduce or eliminate the disadvantages associated with conventional SI joint stabilization systems, apparatus and methods.

It is another object of the invention to provide improved minimally-invasive SI joint stabilization systems and apparatus, and methods of using same, that facilitate posterior placement of bone structure prostheses in and, thereby, stabilization of dysfunctional SI joints.

It is another object of the invention to provide improved minimally-invasive SI joint stabilization systems and apparatus, including improved bone structure prostheses, which, when employed to stabilize dysfunctional SI joints, disrupt less tissue and muscles, and avoid nerves and large blood vessels.

It is another object of the invention to provide improved minimally-invasive SI joint stabilization systems and apparatus, including improved bone structure prostheses, which can be readily employed to stabilize dysfunctional SI joints.

It is another object of the invention to provide improved minimally-invasive SI joint stabilization systems and apparatus, which effectively ameliorate pain associated with SI joint dysfunction.

It is another object of the invention to provide multi-functional bone structure prostheses that can readily be employed in minimally-invasive SI joint stabilization methods.

It is another object of the invention to provide multi-function bone structure prostheses that facilitate remodeling of damaged osseous tissue and regeneration of new osseous tissue and osseous tissue structures.

It is another object of the invention to provide multi-function bone structure prostheses that are adapted to provide neurostimulation of anatomical structures associated with SI joints when implanted therein.

It is another object of the invention to provide multi-function bone structure prostheses that are adapted to deliver biologically active agents and pharmacological agents to bone structures when implanted therein.

It is another object of the invention to provide multi-function bone structure prostheses that are adapted to monitor structural parameters of bone structures when implanted therein.

It is another object of the invention to provide multi-function bone structure prostheses that are adapted to monitor physiological and biomechanical parameters associated with bone structures when implanted therein.

SUMMARY OF THE INVENTION

The present invention is directed to systems, apparatus and methods for treating dysfunctional SI joints.

In one embodiment of the invention, there is thus provided a system for treating dysfunctional SI joints comprising a multi-function bone structure prosthesis adapted to be delivered to and inserted into a dysfunctional SI joint via a posterior approach, the multi-function bone structure prosthesis comprising first and second elongated partially cylindrical sections connected to a bridge section, the bridge section comprising a first tapered region configured and adapted to disrupt at least articular cartilage and cortical bone, the first elongated partially cylindrical section comprising a first elongated partially cylindrical section proximal end, a first elongated partially cylindrical section distal end and a first internal lumen that extends through the first elongated partially cylindrical section, the first internal lumen comprising first internal threads disposed on the first elongated partially cylindrical section proximal end, the second elongated partially cylindrical section comprising a second elongated partially cylindrical section proximal end, a second elongated partially cylindrical section distal end and a second internal lumen that extends through the second elongated partially cylindrical section, the second internal lumen comprising second internal threads disposed on the second elongated partially cylindrical section proximal end, the multi-function bone structure prosthesis further comprising a first prosthesis module adapted to attenuate pain proximate a dysfunctional SI joint when the multi-function bone structure prosthesis is inserted therein, said first prosthesis module adapted to threadably engage at least the first internal threads of the first elongated partially cylindrical section.

In some embodiments of the invention, the multi-function bone structure prosthesis further comprises a second prosthesis module adapted to threadably engage at least the second internal threads of the second elongated partially cylindrical section.

In some embodiments, the second prosthesis module is adapted to monitor at least one physiological parameter associated with the dysfunctional SI joint in vivo when the multi-function bone structure prosthesis is inserted therein.

In some embodiments, the at least one-physiological parameter is selected from the group consisting of temperature proximate said dysfunctional SI joint, electrical activity of at least one muscle proximate said dysfunctional SI joint, and contractile capacity of the at least one muscle proximate said dysfunctional SI joint (including muscle contraction time and maximal radial displacement of the at least one muscle).

In some embodiments, the second prosthesis module is adapted to monitor at least one biokinetic parameter associated with the dysfunctional SI joint in vivo when the multi-function bone structure prosthesis is inserted therein.

In some embodiments, the at least one biokinetic parameter is selected from the group consisting of motion of said dysfunctional SI joint and force exerted proximate said multi-function bone prosthesis and, thereby, said dysfunctional SI joint.

In some embodiments of the invention, at least the first internal lumen of the first elongated partially cylindrical section is adapted to receive an osteogenic composition therein.

In some embodiments of the invention, at least the first elongated partially cylindrical section of the multi-functional bone structure prosthesis further comprises a plurality of slots in communication with the first internal lumen of the first elongated partially cylindrical section, the plurality of slots being configured and adapted to allow the osteogenic composition to be dispersed out of the first internal lumen and delivered to the dysfunctional SI joint when the multi-function bone structure prosthesis is the disposed in the dysfunctional SI joint.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 5 is an exploded side view of the multi-function bone structure prosthesis shown in FIG. 4, in accordance with the invention;

FIG. 6 is a side view of the multi-function bone structure prosthesis shown in FIG. 4 showing the prosthesis module shown in FIG. 3A engaged thereto, in accordance with the invention;

FIG. 7 is an exploded side view of the multi-function bone structure prosthesis shown in FIG. 4 with the prosthesis module shown in FIG. 3B associated therewith, in accordance with the invention;

FIG. 8 is a side view of the multi-function bone structure prosthesis shown in FIG. 4 showing the prosthesis module shown in FIG. 3B engaged thereto, in accordance with the invention;

FIG. 9 is an exploded side view of the multi-function bone structure prosthesis shown in FIG. 4 with the prosthesis module shown in FIG. 3C associated therewith, in accordance with the invention;

FIG. 10 is a side view of the multi-function bone structure prosthesis shown in FIG. 4 showing the prosthesis module shown in FIG. 3C engaged thereto, in accordance with the invention.

DETAILED DESCRIPTION OF THE PREFERRED EMBODIMENT

Figure 1A:
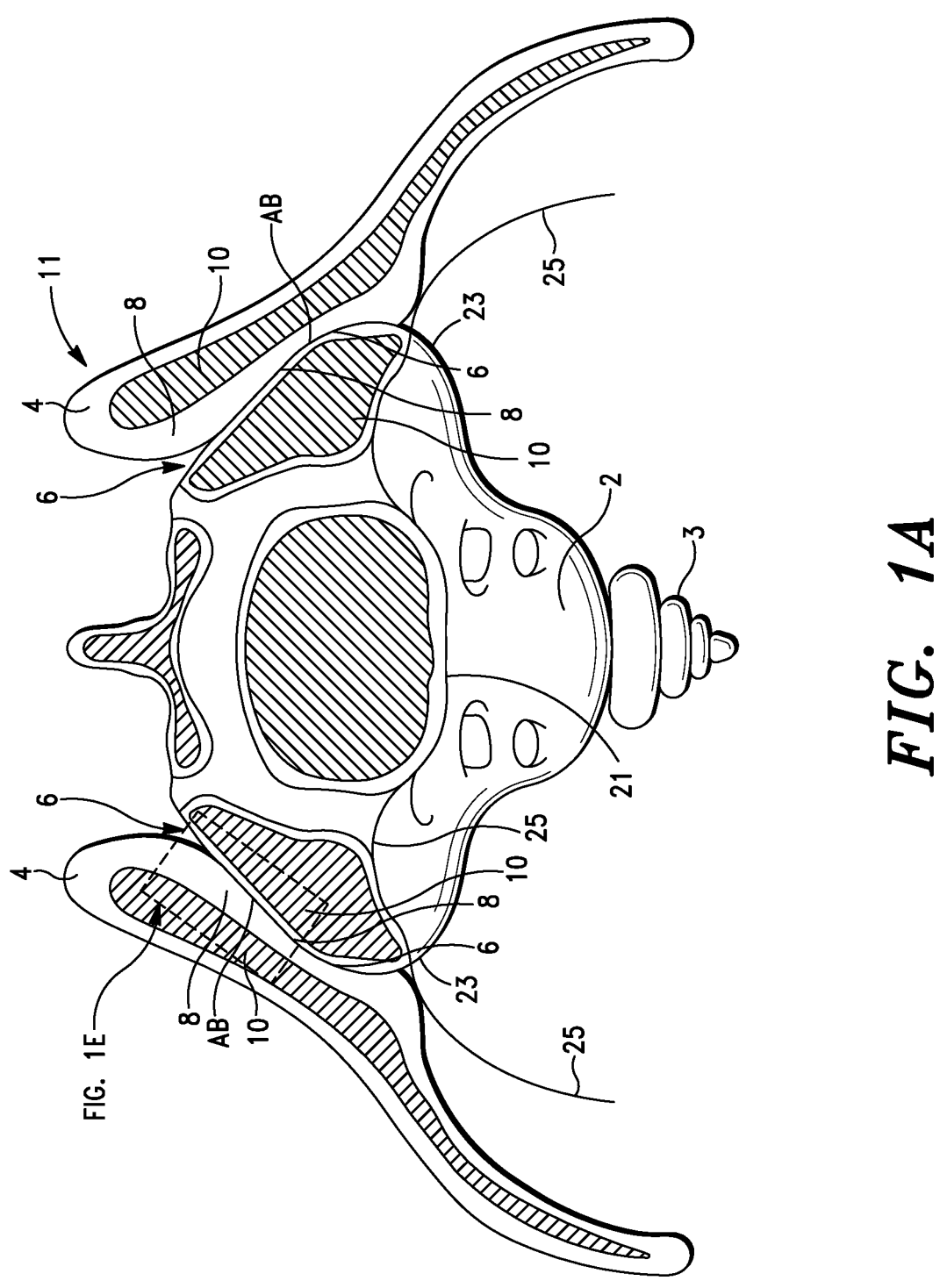
FIG. 1A is a schematic illustration of a human pelvic region from an anteroposterior (AP) perspective showing the SI joints thereof.
Figure 1B:
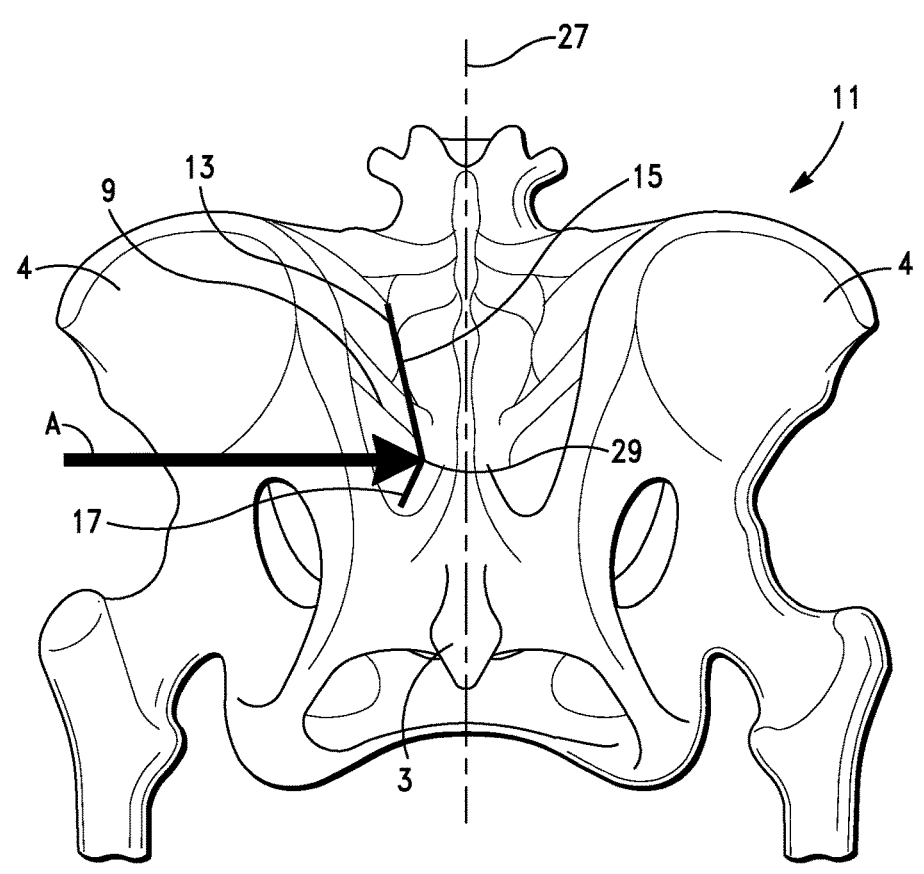
FIG. 1B is another schematic illustration of a human pelvic region from a posterior perspective showing the adjoining sacrum and ilium bone structures, and ligamentous structures thereof.
Figure 1C:
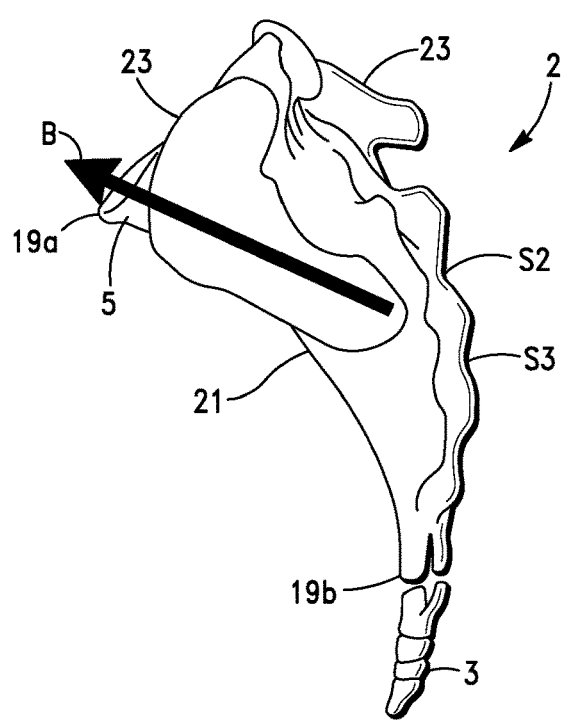
FIG. 1C is a schematic illustration of the sacrum and coccyx from a lateral perspective showing the sacral promontory and the articular surface of sacrum.
Figure 1D:
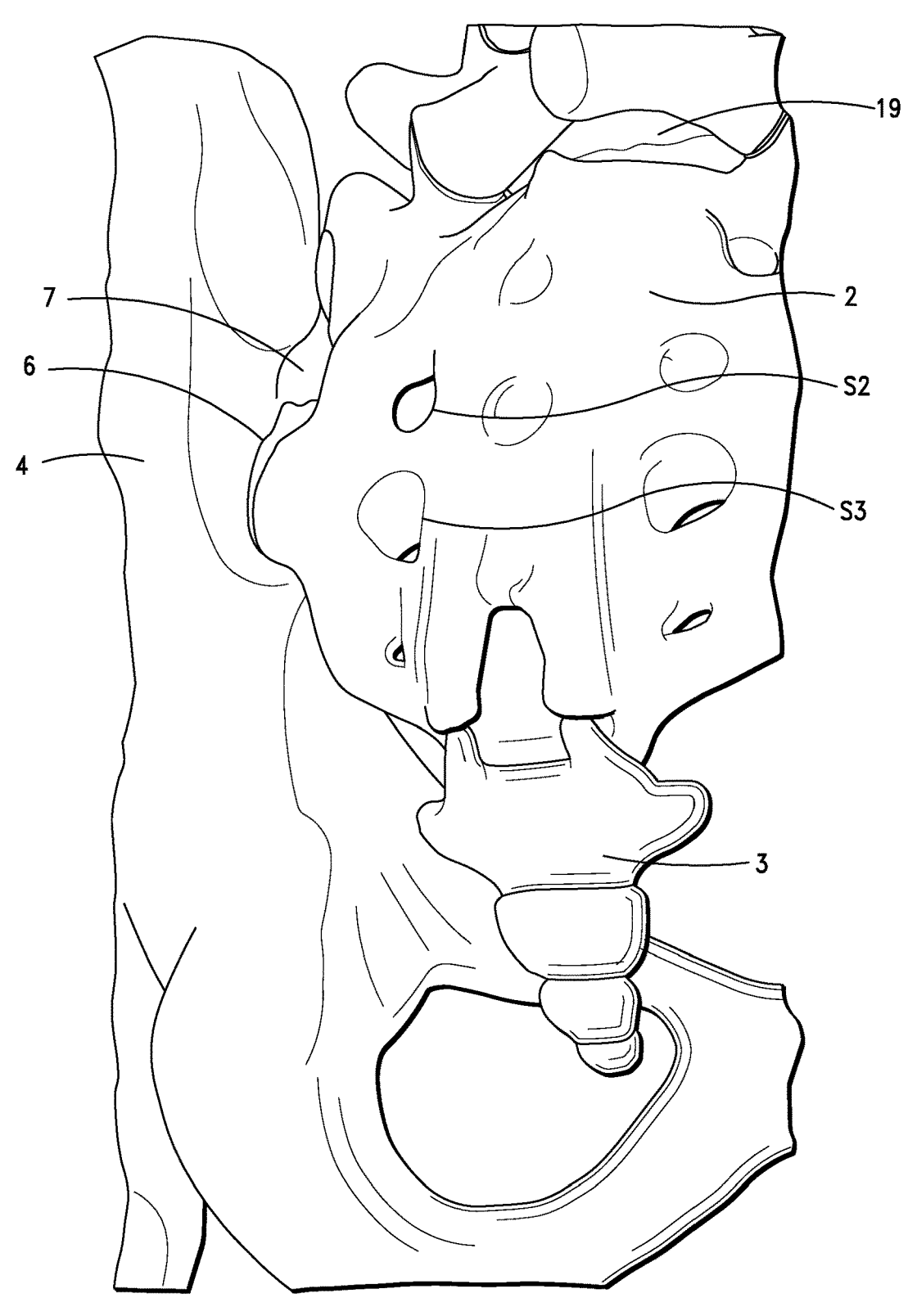
FIG. 1D is another schematic illustration of a human pelvic region from a posterior inferior perspective showing the adjoining sacrum and ilium bone structures of an SI joint, and an SI joint dorsal recess between the sacrum and ilium bone structures.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with sacroiliac (SI) joint stabilization, fixation and fusion procedures, the invention is not limited to such procedures. According to the invention, the systems, apparatus and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures, and mean and include a surface of a bone structure that forms an articulating junction (i.e., a synovial joint) with an adjacent bone structure, e.g., the articular surfaces of the sacrum and ilium bone structures.

The term "SI joint dorsal recess", as used herein, means and includes a recess or space between the sacrum and ilium bone structures proximate the S2 segment region of the sacrum.

The terms "fusion" and "arthrodesis" are used interchangeably herein in connection with bone structures, and mean and include partial or complete immobilization of adjacent bone structures; particularly, the sacrum and ilium bone structures.

The term "stabilization", as used herein, means and includes reinforcing, e.g., supporting, or modulating motion of adjacent articular bone structures; particularly, the sacrum and ilium bone structures. The term "stabilization", thus, in some instances, means and includes fusion and arthrodesis of adjacent bone structures.

The term "neurostimulation", as used herein, means and includes modulation of a subject's nervous system via electrical or electromagnetic stimulation to modulate or attenuate the subject's pain.

The term "prosthesis", as used herein in connection with bone structures, means and includes a system or apparatus configured and adapted to stabilize or modulate motion of articulating bone structures; particularly, the sacrum and ilium bone structures. The term "prosthesis" thus includes a SI joint prosthesis adapted to stabilize a dysfunctional SI joint.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly($\varepsilon$-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including FocalSeal®, Progel™ Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)), and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2), and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs), and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab; disease-modifying anti-rheumatic drugs (DMARDs), including methotrexate and hydroxychloroquine; antibiotics, anti-viral agents, steroidal anti-inflammatories, non-steroidal anti-inflammatories, anti-thrombotic agents, including anti-coagulants and anti-plate-let agents; and vasodilating agents.

The terms "pharmacological agent" and "active agent" further mean and include, without limitation, the following bisphosphonate agents and compositions comprising same: risedronate (Actonel®), alendronate (Fosamax®), ibandro-nate (Boniva®), zoledronic acid (Reclast®), pamidronate (Aredia®), and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, ami-kacin, aminoglycosides, cephalosporins, clindamycin, erythromycin, fluoroquinolones, macrolides, azolides, met-ronidazole, trimethoprim-sulfamethoxazole, polymyxin B, oxytetracycline, tobramycin, cefazolin, and rifampin.

The terms "anti-inflammatory" and "anti-inflammatory agent" are also used interchangeably herein, and mean and include a "pharmacological agent", which, when a thera-peutically effective amount is administered to a subject, prevents or treats bodily tissue inflammation, i.e., the pro-tective tissue response to injury or destruction of tissues, which serves to destroy, dilute, or wall off both the injurious agent and the injured tissues.

Anti-inflammatory agents thus include, without limita-tion, dexamethasone, betamethasone, prednisone, predniso-lone, methylprednisolone sodium succinate, methylpred-nisolone, cortisone, ketorolac, diclofenac, and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molyb-denum particles, lead particles, and mixtures thereof.

As indicated above, the term "pharmacological composi-tion", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchange-ably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or character-istic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute complete-ness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appre-ciation for the inventive principles and advantages thereof, rather than to limit in any manner the invention. The invention is defined solely by the appended claims, includ-ing any amendments made during the pendency of this application, and all equivalents of those claims as issued.

As indicated above, the present invention is directed to minimally-invasive systems, apparatus and methods for treating dysfunctional bone structures; particularly, dysfunc-tional SI joints.

In some embodiments of the invention, there are thus provided minimally-invasive systems for treating dysfunc-tional SI joints comprising multi-functional bone structure prostheses.

In a preferred embodiment of the invention, the multi-functional bone structure prostheses of the invention are configured and adapted to be delivered to dysfunctional SI joints to stabilize and treat the joints via a posterior approach.

As indicated above, SI joint stabilization (and, hence, treatment), including minimally-invasive SI joint stabiliza-tion, typically comprises surgical placement of a bone structure prosthesis proximate to or in a dysfunctional SI joint via anterior, lateral and posterior approaches to the SI joint.

From the perspective of FIG. 1A, an anterior approach to the SI joint 6 (and, hence, a dysfunctional SI joint) would be substantially perpendicular to the page upon which FIG. 1A is printed.

Figure 1E:
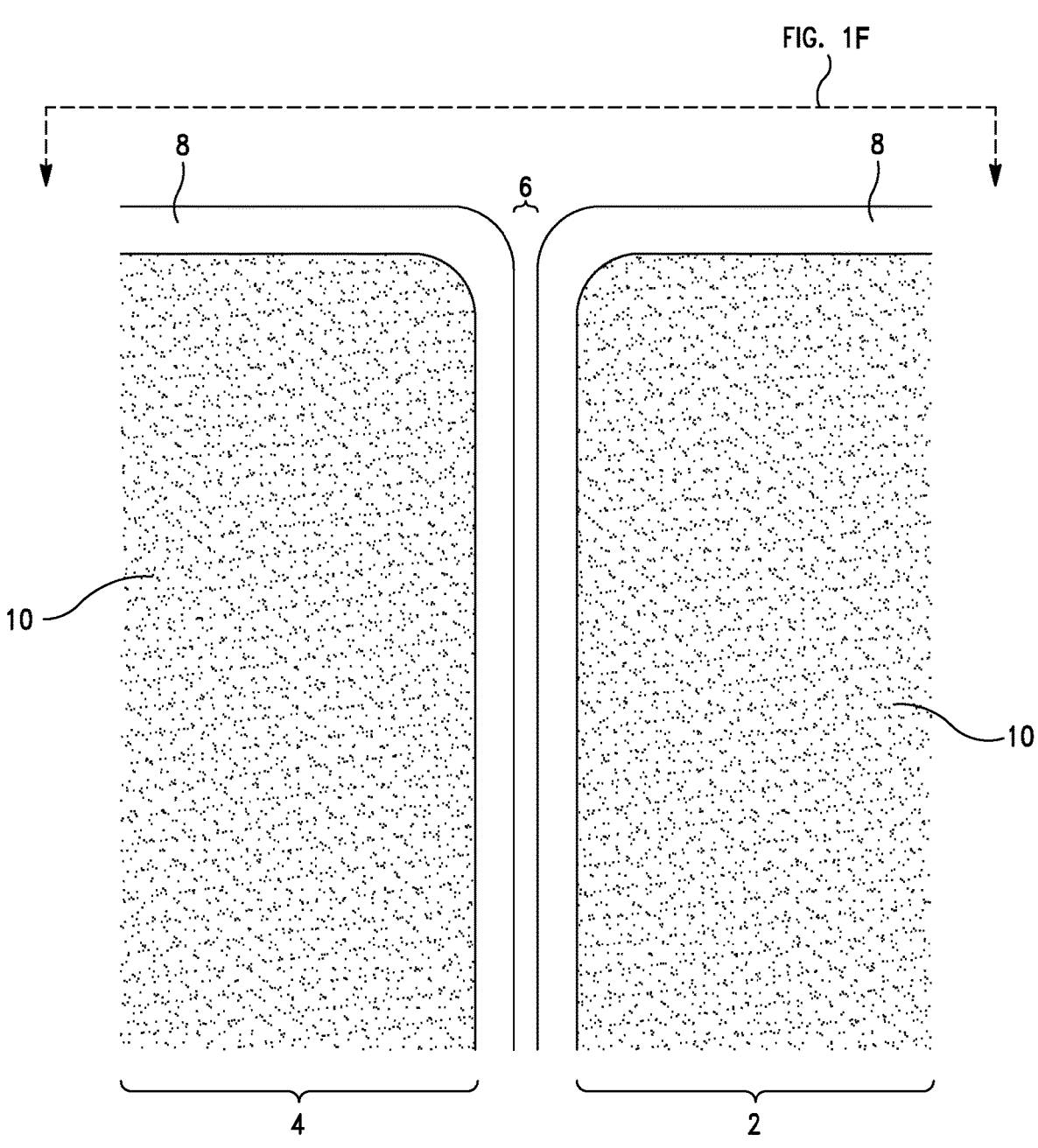
FIG. 1E is an illustration of a SI joint from a superior perspective showing the adjoining sacrum and ilium articular surfaces.

Referring now to FIG. 1E there is shown an illustration of a SI joint 6 and surrounding structures. For illustrative simplicity, a uniform layer of cortical bone 8 is shown adjacent a deeper layer of trabecular bone 10 on both of the depicted sacrum 2 and ilium 4 structures. However, in actuality, such layers are far less uniform and homogeneous.

Figure 1F:
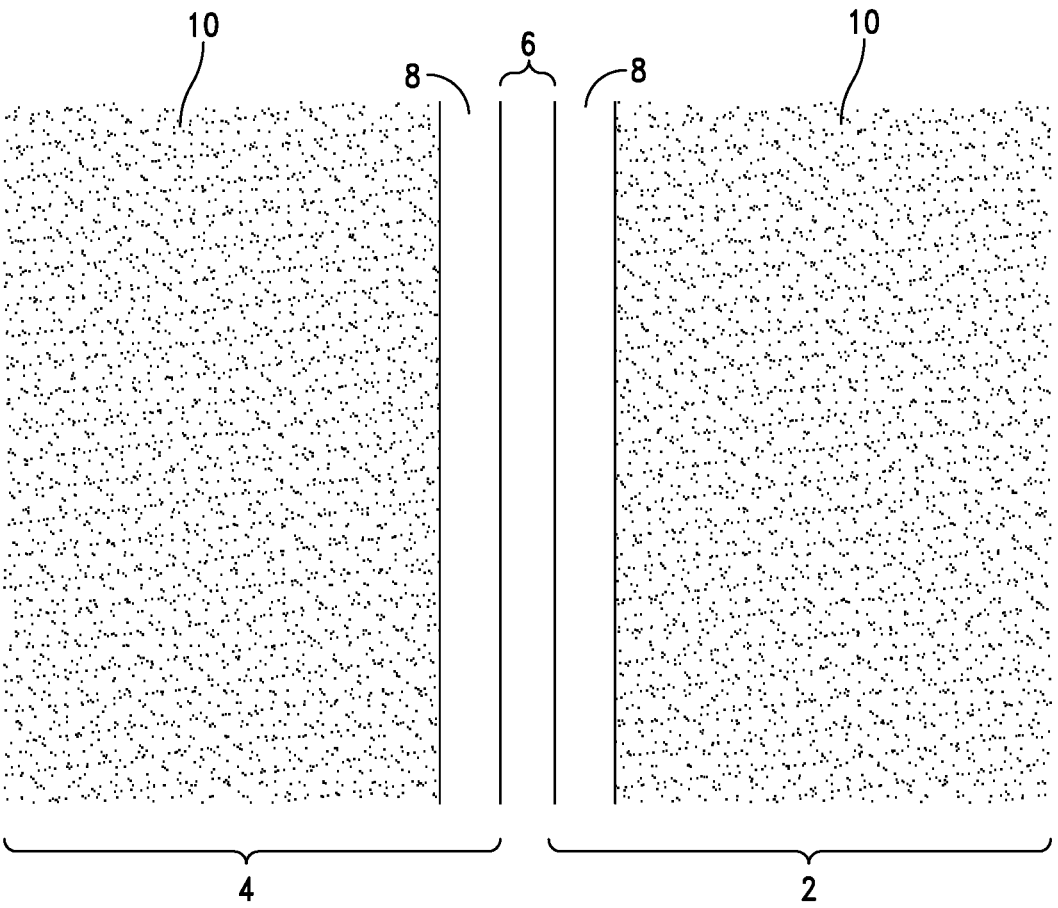
FIG. 1F is another illustration of a SI joint from a posterior perspective showing the adjoining sacrum and ilium articular surfaces.
Figure 1G:
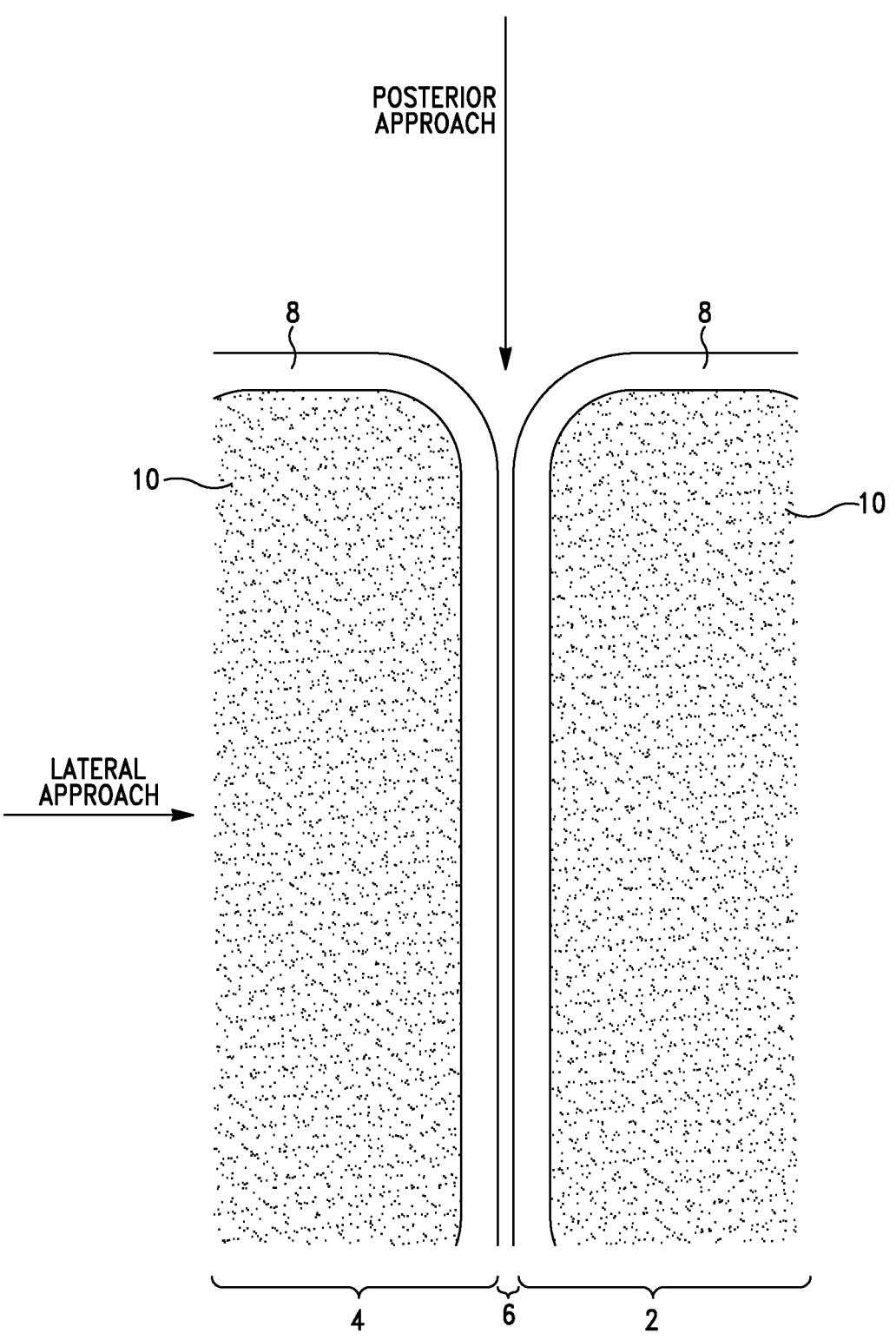
FIG. 1G is a further illustration of the SI joint shown in FIG. 1F showing lateral and posterior approaches to the SI joint, in accordance with the invention.

Referring now to FIG. 1F, there is shown a view of the same structure from a different posterior perspective. From the perspective of FIG. 1F, a posterior approach to the SI joint 6 (and, hence, a dysfunctional SI joint) would be substantially perpendicular to the page upon which FIG. 1F is printed. Indeed, referring to FIG. 1G, a variation similar to that depicted in FIG. 1E is illustrated, showing an approximate approach vector for a lateral approach to the SI joint 6 versus a posterior approach, using the orientation paradigms introduced in FIGS. 1A and 1F-1G. Such paradigms are used to illustrate various embodiments of the subject invention in various figures that follow FIGS. 1A and 1F-1G.

As indicated above, a major disadvantage associated with many conventional anterior or lateral approaches to a dysfunctional SI joint is that muscles and ligaments are typically disrupted and often damaged. Nerves and blood vessels are also susceptible to damage during such SI joint stabilization methods.

In contrast, posterior delivery of the bone structure prostheses of the invention to a dysfunctional SI joint is much less invasive. Indeed, less tissue and fewer muscles are disrupted, and nerves and large blood vessels are avoided.

Thus, as indicated above, the multi-functional bone structure prostheses of the invention are configured and adapted to be delivered to and inserted into dysfunctional SI joints via a posterior approach.

Referring now to FIGS. 2A-2F, there is shown one embodiment of a multi-function bone structure prosthesis of the invention.

Although the multi-function bone structure prosthesis (denoted "70a") is described in connection with stabilizing and, hence, treating a dysfunctional SI joint, according to the invention, the multi-function bone structure prosthesis 70a can also be employed to stabilize other articulating and non-articulating bone structures, including individual skeletal members.

Figures 2A, 2B:
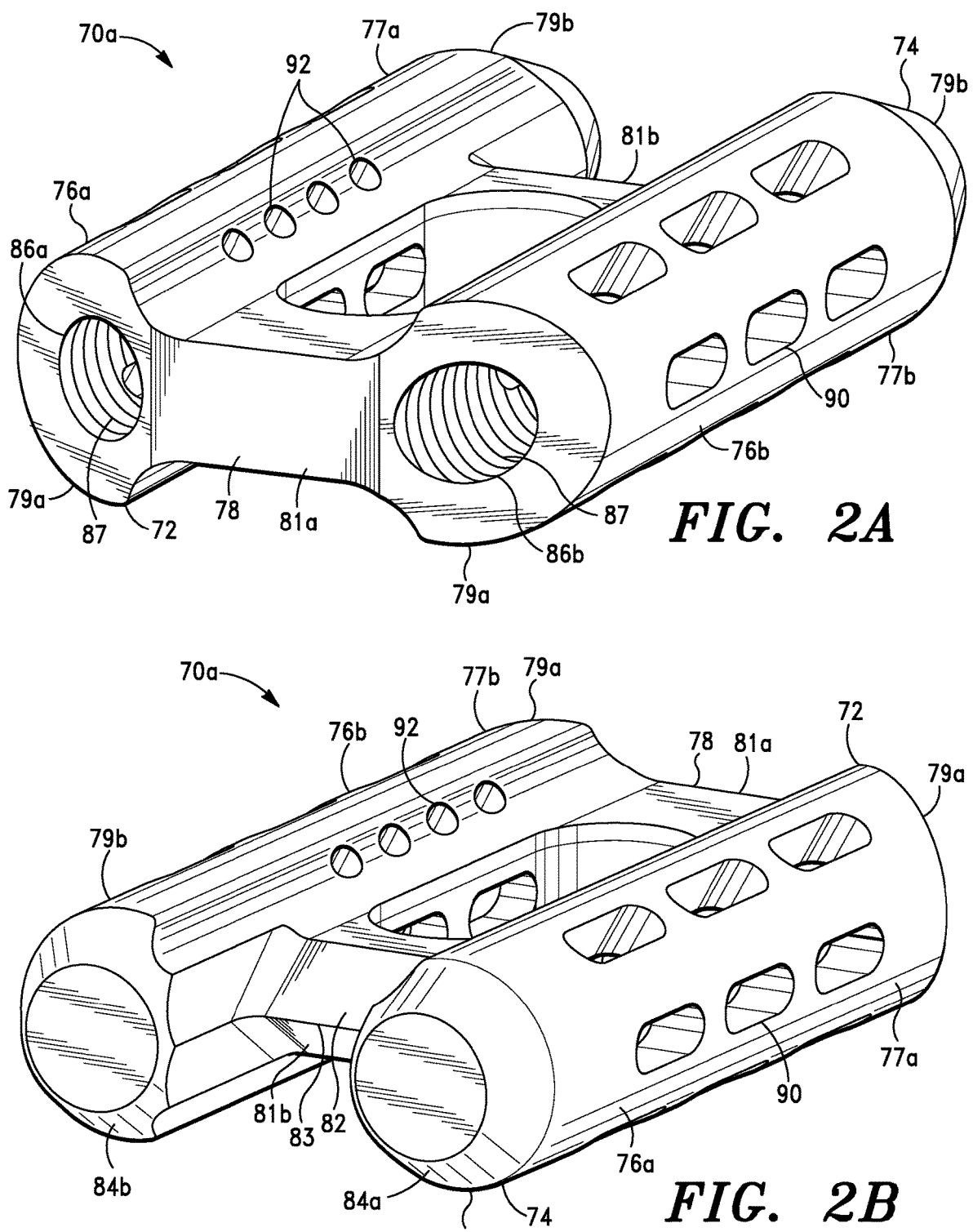
FIG. 2A is a perspective view of one embodiment of a SI joint prosthesis, in accordance with the invention.
FIG. 2B is a further perspective view of the SI joint prosthesis shown in FIG. 2A, in accordance with the invention.

As illustrated in FIGS. 2A and 2B, the multi-function bone structure prosthesis 70a (referred to hereinafter as "SI joint prosthesis" and/or "multifunction SI joint prosthesis") comprises a biocompatible and, hence, implantable member comprising proximal and distal ends 72, 74, and first and second elongated partially cylindrical sections 76a, 76b connected to a bridge section 78, whereby the SI joint prosthesis 70a comprises a continuous exterior surface comprising first and second partially cylindrical surface regions 77a, 77b.

As further illustrated in FIGS. 2A and 2B, the first and second partially cylindrical sections 76a, 76b comprise proximal and distal ends 79a, 79b. The bridge section 78 similarly comprises proximal and distal ends 81a, 81b.

As set forth in Co-pending U.S. application Ser. Nos. 17/469,132, 17/468,811, 17/463,831, and 17/834,392, the SI joint prosthesis 70a can comprise any suitable length from the proximal ends 79a to the distal ends 79b of the partially cylindrical sections 76a, 76b. In some embodiments, the prosthesis 70a comprises a length in the range of 20-50 mm, more preferably, a length in the range of 30-40 mm.

As further set forth in Co-pending U.S. application Ser. Nos. 17/469,132, 17/468,811, 17/463,831, and 17/834,392, the first partially cylindrical surface region 77a preferably comprises a partially cylindrical surface region shape that corresponds to at least a first portion of a pilot SI joint opening in the dysfunctional SI joint, and the second partially cylindrical surface region 77b similarly preferably comprises a partially cylindrical surface region shape that corresponds to at least a second portion of the pilot SI joint opening in the dysfunctional SI joint.

As illustrated in FIG. 2B, the distal end 81b of the bridge section 78 preferably comprises a taper region 82, which is configured and adapted to disrupt, i.e., cut into and through, articular cartilage and cortical bone 8 (and, in some aspects, trabecular bone 10), which define a SI joint.

As further illustrated in FIG. 2B, the distal ends 79b of the first and second elongated partially cylindrical sections 76a, 76b also preferably comprise tapered regions 84a, 84b, which facilitate insertion of the distal ends 79b of the first and second elongated partially cylindrical sections 76a, 76b into dysfunctional SI joints.

Figure 2C:
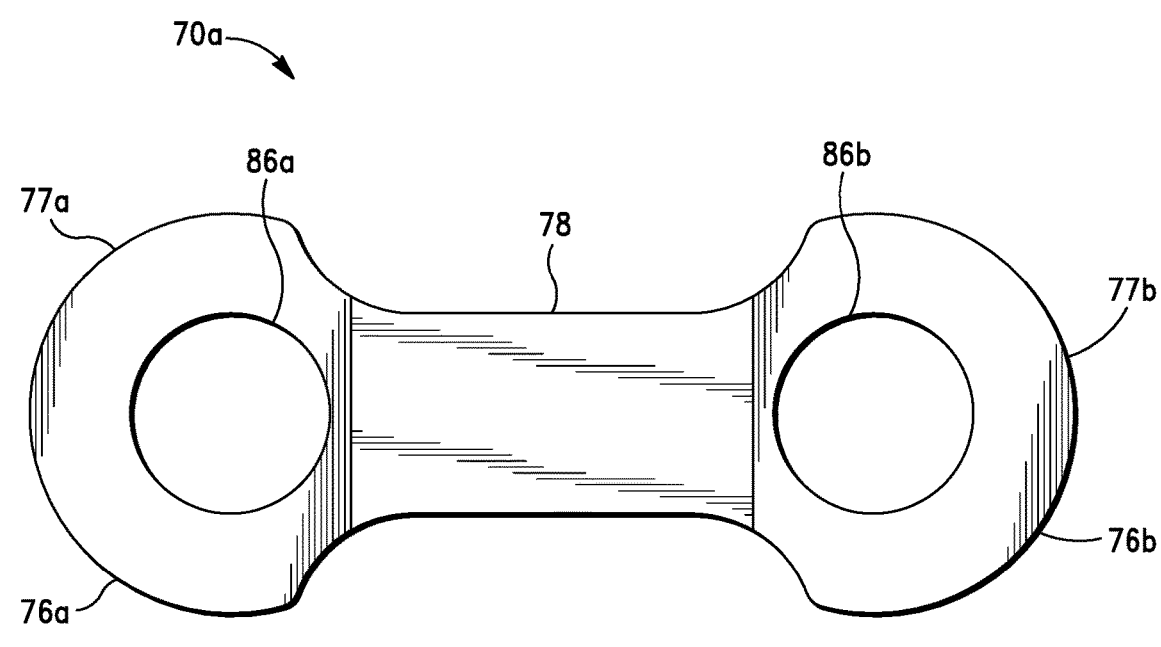
FIG. 2C is a rear plan view of the SI joint prosthesis shown in FIG. 2A, in accordance with the invention.
Figure 2D:
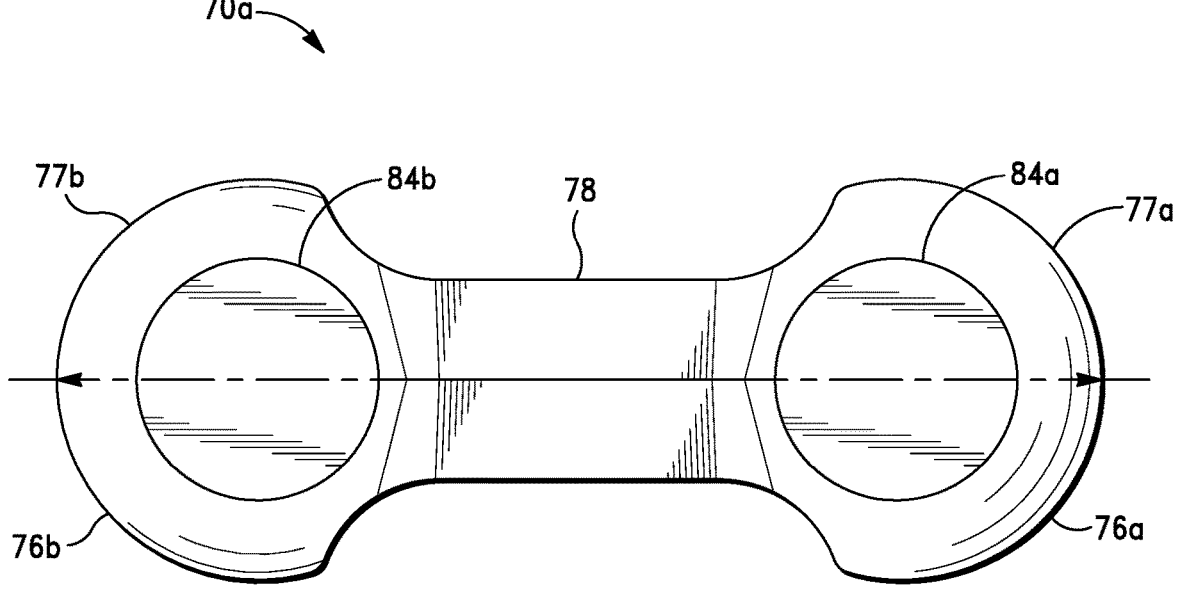
FIG. 2D is a front plan view of the SI joint prosthesis shown in FIG. 2A, in accordance with the invention.
Figures 2E, 2F:
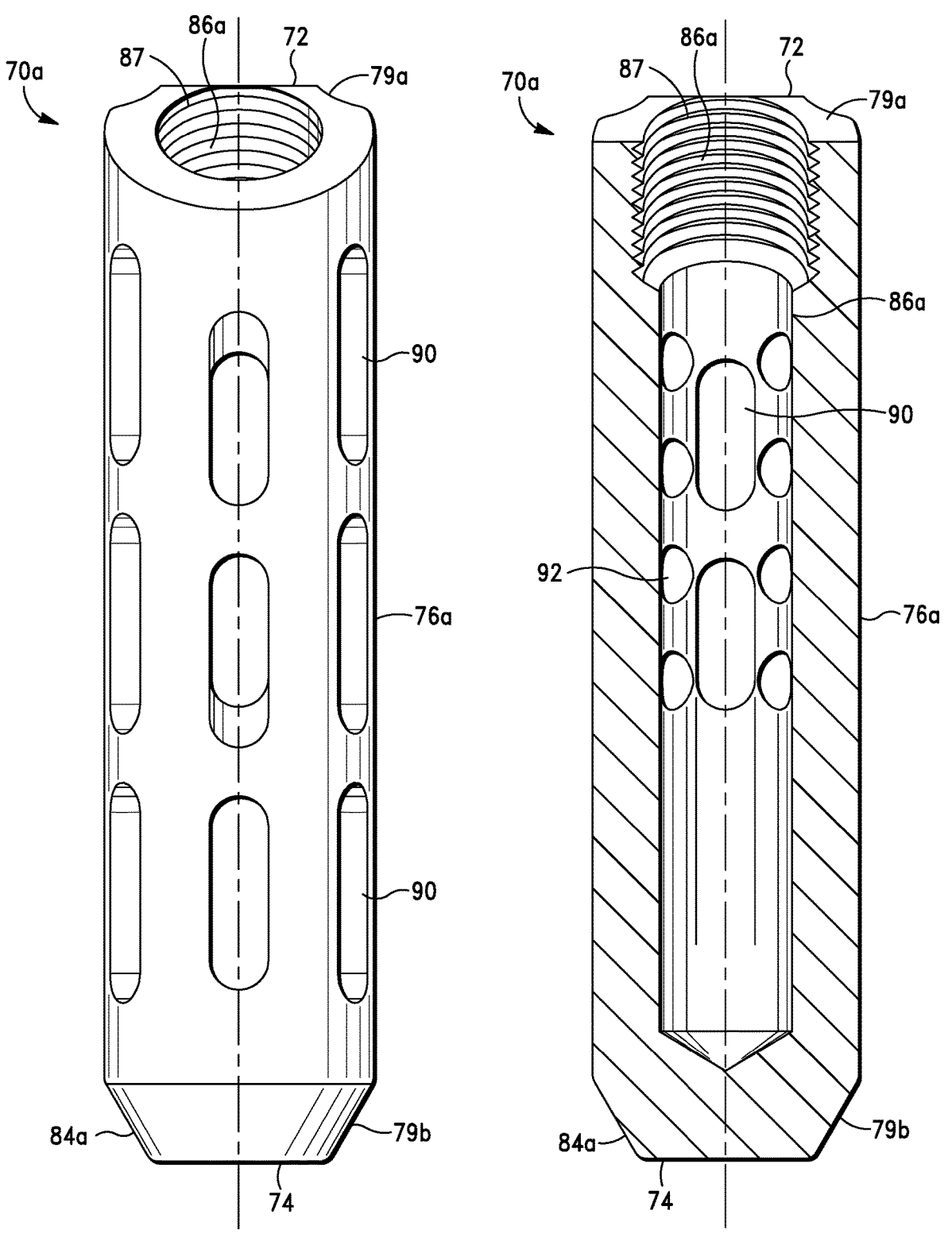
FIG. 2E is a right-side plan view of the SI joint prosthesis shown in FIG. 2A, in accordance with the invention.
FIG. 2F is a right-side sectional plan view of the SI joint prosthesis shown in FIG. 2A, in accordance with the invention.

As illustrated in FIGS. 2A, 2C, and 2F, the first elongated partially cylindrical section 76a of the SI joint prosthesis 70a comprises an internal prosthesis engagement member lumen 86a that extends from the proximal end 79a of the first elongated partially cylindrical section 76a.

As further illustrated in FIGS. 2A and 2C, the second elongated partially cylindrical section 76b of the SI joint prosthesis 70a also comprises an internal prosthesis engagement member lumen 86b that extends from the proximal end 79a of the first elongated partially cylindrical section 76b.

As further illustrated in FIG. 2A, in a preferred embodiment of the invention, the internal prosthesis engagement member lumens 86a, 86b of the first and second elongated partially cylindrical sections 76a, 76b comprise internal threaded regions 87 adapted to engage a prosthesis deployment assembly, which, as set forth in Co-pending U.S. application Ser. No. 17/463,831, is adapted to deliver the SI joint prosthesis 70a to a dysfunctional SI joint, and at least one prosthesis module of the invention, which is discussed in detail below.

In a preferred embodiment, the internal prosthesis engagement lumens 86a, 86b are also configured to receive agents and compositions that further facilitate adhesion of the SI joint prosthesis 70a to and, hence, in SI joints. Such agents and compositions are set forth in in Co-pending U.S. application Ser. No. 17/463,831.

In a preferred embodiment, the internal prosthesis engagement lumens 86a, 86b are also configured to receive one or more the aforementioned biologically active agents and compositions, including osteogenic agents and compositions, and pharmacological agents and compositions that promote or induce proliferation, and/or growth and/or remodeling and/or regeneration of osseous tissue and/or facilitate osseous tissue ingrowth into the SI joint prosthesis 70a when the SI joint prosthesis 70a is disposed in a dysfunctional SI joint, whereby, the SI joint prosthesis 70a comprises a dual or multi-function SI joint prosthesis, i.e., a prosthesis adapted to at least (i) stabilize a dysfunctional SI joint and (ii) induce proliferation, and/or growth and/or remodeling and/or regeneration of osseous tissue and, thereby, healing and arthrodesis of the dysfunctional SI joint when implanted therein.

Referring back to FIGS. 2A and 2B, in a preferred embodiment, the SI joint prosthesis 70a further comprises a plurality of slots 90 and apertures 92, which preferably are in communication with the internal prosthesis engagement member lumens 86a, 86b.

In a preferred embodiment, the apertures 92 are sized and configured to allow the adhesive compositions and/or biologically active agent compositions and/or pharmacological agent compositions to be dispersed out of the internal prosthesis engagement member lumens 86a, 86b when the SI joint prosthesis 70a is disposed therein.

As set forth in Co-pending U.S. application Ser. Nos. 17/469,132, 17/468,811, 17/463,831, and 17/834,392, the SI joint prosthesis 70*a* can comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

The SI joint prosthesis 70*a* can additionally comprise a porous structure to facilitate (i) adhesion of the prosthesis 70*a* to SI joint bone structures, i.e., sacrum and ilium bone structures, and (ii) bone or osseous tissue ingrowth into the prosthesis 70*a*.

As further set forth in Co-pending U.S. application Ser. Nos. 17/469,132, 17/468,811, 17/463,831, and 17/834,392, the SI joint prosthesis 70*a* can further comprise an outer coating.

According to the invention, the outer coating can comprise one of the aforementioned osteogenic compositions, one of the aforementioned biologically active agent compositions or one of the aforementioned pharmacological agent compositions.

According to the invention, the outer coating can further comprise a biocompatible adhesive composition, such as, without limitation, poly(L-glutamic acid)-based compositions, poly(γ-glutamic acid)-based compositions, poly(alkyl cyano acrylate)-based compositions, and polyacrylic acid-based compositions.

In some embodiments, the outer coating comprises one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

As set forth in Applicant's Co-Pending U.S. application Ser. Nos. 17/469,132, 17/468,811, 17/463,831, and 17/834,392, PGS and derivatives thereof possess a unique property of inducing remodeling of damaged osseous or bone tissue and, hence, healing of the associated bone structures when disposed proximate thereto.

A further seminal property of PGS is that its physical state can be modulated during synthesis by controlling the "degree of esterification" via at least one crosslinking agent, e.g., methylene diphenyl diisocyanate (MDI), whereby the PGS exhibits adhesive properties.

As further set forth in Co-pending U.S. application Ser. Nos. 17/469,132, 17/468,811, 17/463,831, and 17/834,392, PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS outer coatings and PGS and PGSA based compositions further comprise one or more of the aforementioned biologically active or pharmacological agents.

To further enhance the functionality of the multi-function SI joint prosthesis 70*a* shown in FIGS. 2A-2F, in a preferred embodiment, the multi-function SI joint prosthesis of the invention, further comprises one or more prosthesis modules (now denoted multi-function SI joint prosthesis "70*b*").

As discussed in detail below, the prosthesis modules are adapted to, among other features, attenuate pain associated with a dysfunctional SI joint and associated structures, monitor physiological and/or biomechanical parameters associated with the dysfunctional SI joint, and induce (or further induce) proliferation, and/or growth and/or remodeling and/or regeneration of osseous tissue and, thereby, healing and arthrodesis of the dysfunctional SI joint when implanted therein.

According to the invention, the prosthesis modules can thus comprise various members or devices, including, without limitation:

a wireless neurostimulation device;

a wireless sensor system that is programmed and configured to monitor biokinetic or biomechanical parameters, e.g., force and motion parameters, and/or physiological parameters proximate an implanted prosthesis;

a biodegradable or bioabsorbable member comprising an osteogenic or pharmacological agent composition;

a biodegradable or bioabsorbable member comprising a sintered bone graft material, which can also include a pharmacological and/or biological agent;

a fenestrated member comprising an osteogenic and/or pharmacological agent, such as a chemotaxis-promoting agent; and a pharmacological agent delivery member that is configured and adapted to continuously deliver pharmacological agents directly to bone structures to, for example, provide localized treatment of malignant growths proximate osseous tissue, e.g., chondrosarcomas (a malignant growth of cartilage-producing cells commonly found proximate to the pelvic region).

According to the invention, the prosthesis modules can comprise various sizes and configurations.

According to the invention, the prosthesis modules comprising a sensor system and a fenestrated member can comprise various biocompatible materials, including any of the aforementioned biocompatible materials.

In some embodiments, the prosthesis modules comprise one of the aforementioned polymers.

As indicated above, in some embodiments, the prosthesis modules comprise one of the aforementioned osteogenic compositions.

As further indicated above, in some embodiments, the prosthesis modules comprise a sintered or compressed bone graft material.

In some embodiments, the prosthesis modules comprise one of the aforementioned outer coatings.

Figures 3A, 3B, 3C, 3D:
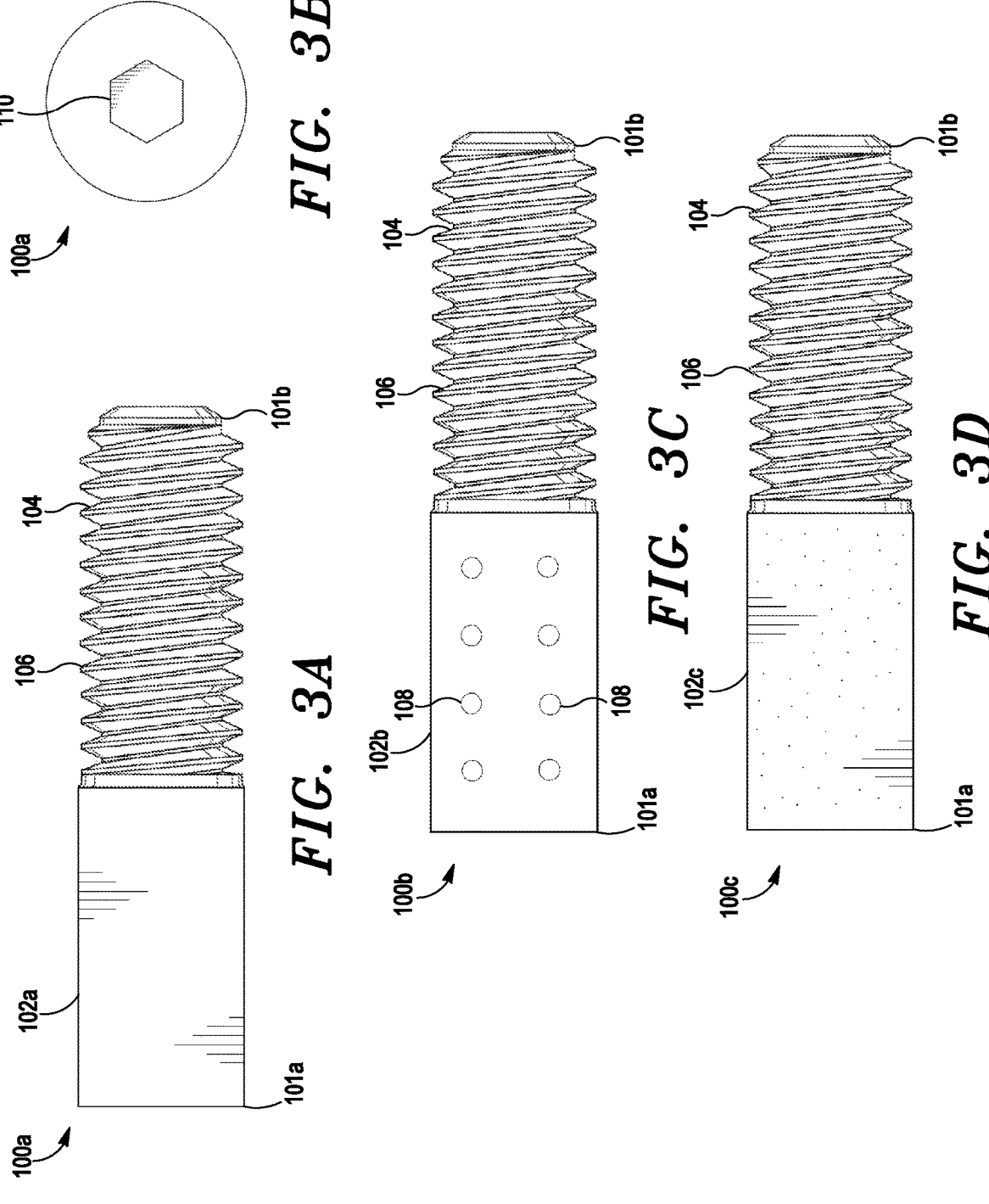
FIG. 3A is a front plan view of one embodiment of a prosthesis module, in accordance with the invention.
FIG. 3B is a top plan view of the prosthesis module shown in FIG. 3A, in accordance with the invention.
FIGS. 3C and 3D are front plan views of further embodiments of prosthesis modules, in accordance with the invention.

Referring now to FIGS. 3A and 3B, there is shown one embodiment of a prosthesis module of the invention, which, according to the invention, can comprise a wireless neurostimulation or sensor system.

According to the invention, the wireless sensor system can comprise various apparatus and systems adapted to monitor biokinetic or biomechanical parameters, such as, without limitation, force, and motion parameters, and/or physiological parameters proximate an implanted prosthesis and, hence, dysfunctional SI joint (or other bone structure).

In some embodiments, the sensor system comprises an apparatus or system adapted to monitor forces exerted proximate an implanted prosthesis and, hence, dysfunctional SI joint (or other bone structure). According to the invention, suitable force monitoring apparatus and systems can comprise, without limitation, a pressure sensor and strain sensor (also referred to as a strain gauge), and like sensors.

In some embodiments, the sensor system comprises an apparatus or system adapted to monitor motion proximate an implanted prosthesis and, hence, dysfunctional SI joint (or other bone structure). According to the invention, suitable motion monitoring apparatus and systems can comprise, without limitation, three-axis accelerometers and like sensors.

In some embodiments, the sensor system comprises an apparatus or system adapted to monitor physiological parameters proximate an implanted prosthesis and, hence, dysfunctional SI joint (or other bone structure). According to the invention, suitable physiological parameter monitoring apparatus and systems can comprise, without limitation, a temperature or thermistor sensor.

According to the invention, suitable physiological parameter monitoring apparatus and systems can also comprise, without limitation, an apparatus or system adapted to monitor physical capacity of muscles, e.g., electromyogram sensor; blood parameters, e.g., a blood oxygen (SpO$_2$) sensor, and musculoskeletal parameters proximate an implanted prosthesis and, hence, dysfunctional SI joint (or other bone structure).

According to the invention, the wireless sensor system can comprise an array of sensors comprising a combination of the aforementioned sensors.

In some embodiments, the neurostimulation and sensor systems comprise a wireless communication system electronically connected to an external electronic device, e.g., a smartphone, tablet, or laptop, wherein output signals from the neurostimulation and sensor systems are transmitted to the external device and, in some embodiments, parameters represented by the output signals are stored and displayed on the external electronic device.

According to the invention, the neurostimulation and sensor systems can comprise any suitable wireless communication system or protocol, including systems that conform to the Bluetooth® standard, ultra-wide band communication protocols, narrow band communication protocols, and near-field communication (NFC) protocols, to connect to any standard smartphone, tablet, or laptop.

Referring back to FIG. 3A, the prosthesis module 100a comprises proximal and distal ends 101a, 101b, a head region 102a disposed proximate the proximal end 101a, and a threaded end region 104 disposed proximate the distal end 101b.

In a preferred embodiment, the head region 102a of the prosthesis module 100a comprises an internal region that is adapted to receive a neurostimulation apparatus or one of the aforementioned sensor systems.

Figure 4:
FIG. 4 is an exploded perspective view of one embodiment of a multi-function bone structure prosthesis, in accordance with the invention.

As illustrated in FIGS. 4-6, in a preferred embodiment, the prosthesis module 100a is sized and configured to engage and be translated into the internal prosthesis engagement member lumens 86a, 86b of the first and second elongated partially cylindrical sections 76a, 76b.

Figure 11:
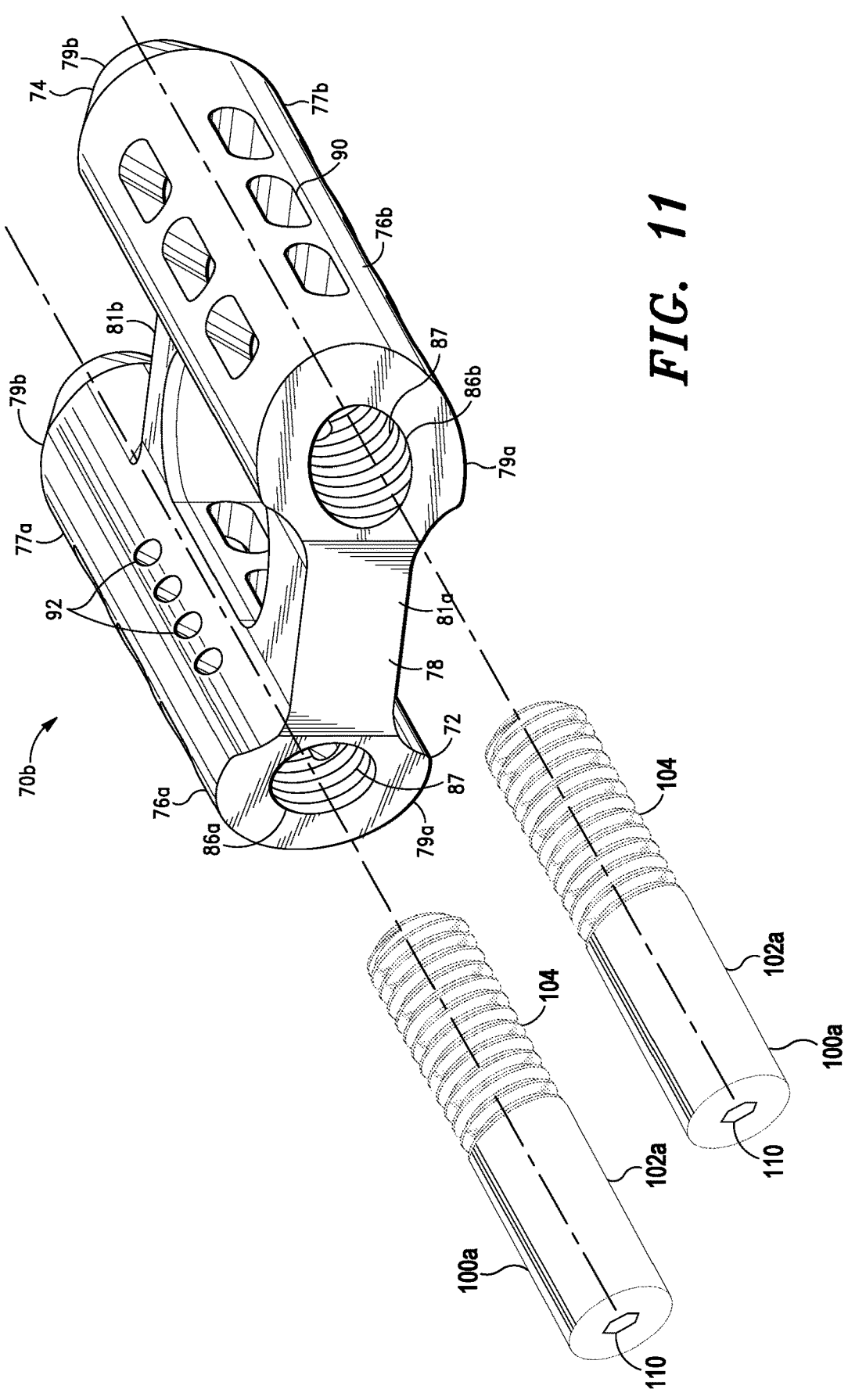
FIGS. 11-13 are exploded perspective views of further embodiments of multi-function bone structure prostheses, in accordance with the invention.
Figure 12:
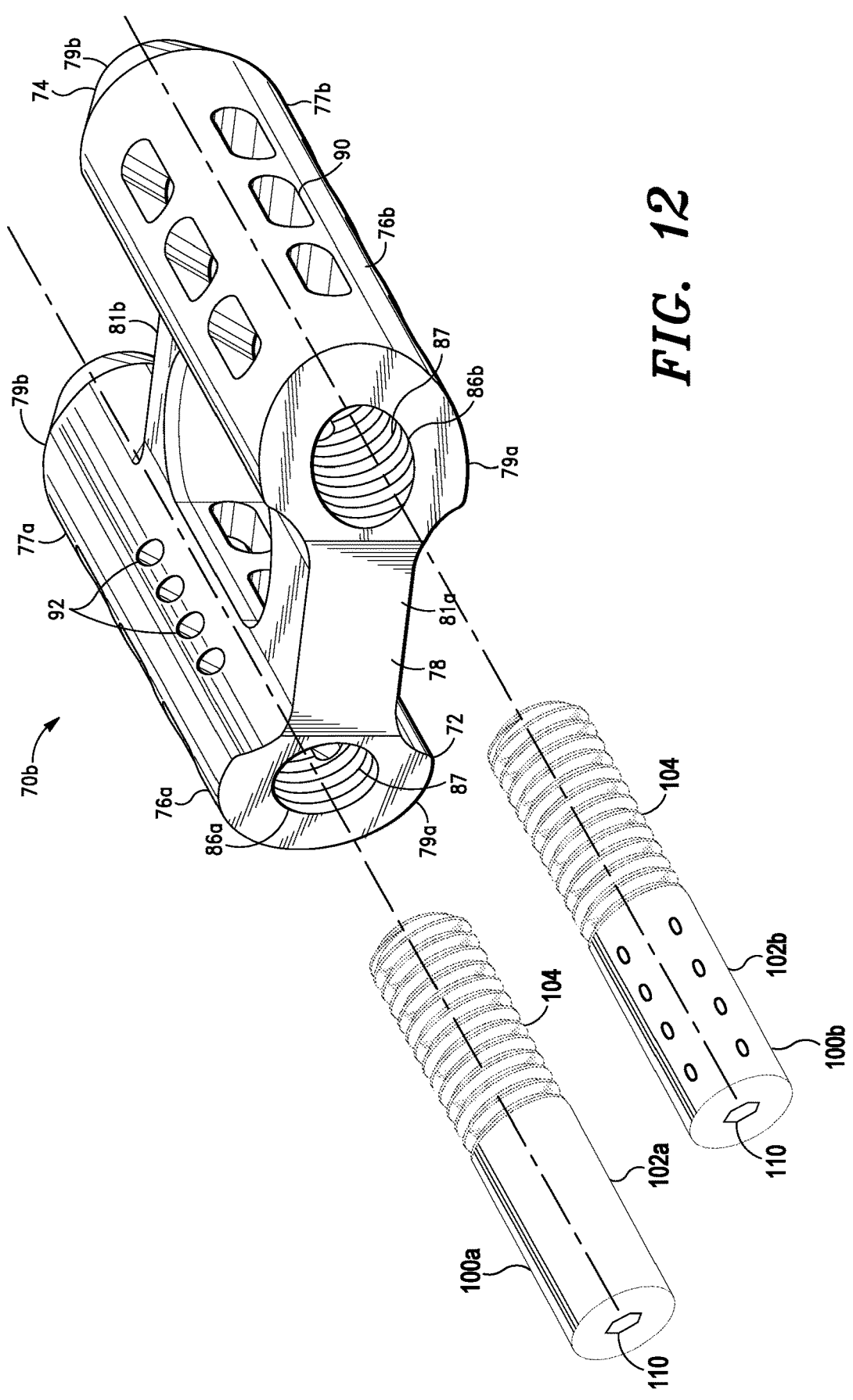
Figure 13:
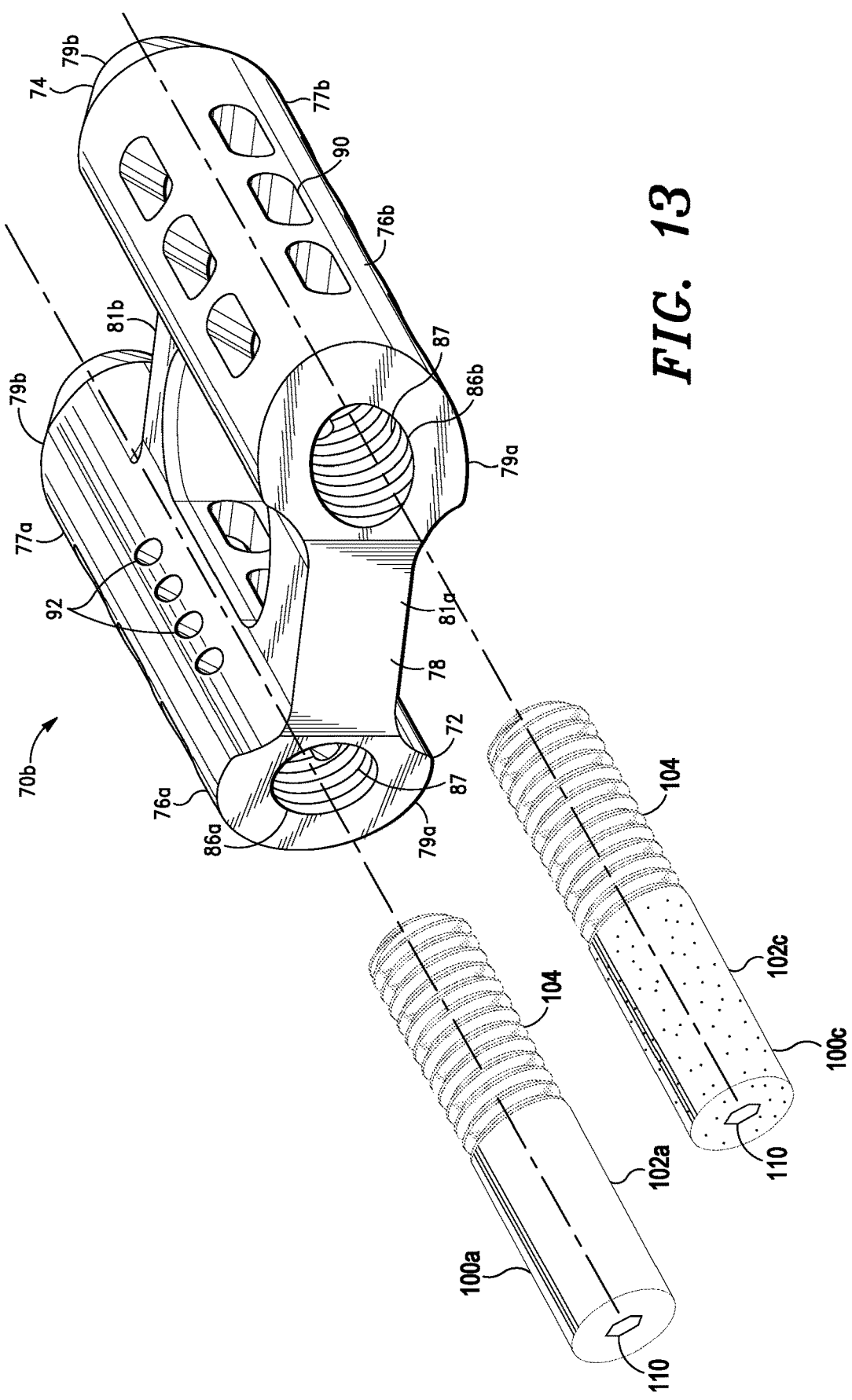

In a preferred embodiment, the prosthesis module 100a is configured, whereby, when the prosthesis module 100a is engaged to the multi-function SI joint prosthesis 70b as described above, the threaded end region 104 is disposed in the internal prosthesis engagement member lumen 86a of the first elongated partially cylindrical section 76a, such as illustrated in FIG. 6, or in the internal prosthesis engagement member lumen 86b of the second elongated partially cylindrical section 76b, and, thus, when two (2) prosthesis modules 100a or two (2) different modules, e.g., prosthesis module 100a and prosthesis module 100b, as discussed below, are engaged to the multi-function SI joint prosthesis 70b, as illustrated in FIGS. 11-13, the threaded end region 104 of the first prosthesis module, i.e., prosthesis module 100a, 100b, or 100c, is disposed in the internal prosthesis engagement member lumen 86a of the first elongated partially cylindrical section 76a and the second prosthesis module i.e., prosthesis module 100a, 100b, or 100c, is disposed in the internal prosthesis engagement member lumen 86b of the second elongated partially cylindrical section 76b.

As further illustrated in FIG. 3A, in a preferred embodiment of the invention, the threaded end region 104 of the prosthesis module 100a comprises at least one thread 106 that is sized and configured to cooperate with the internal threaded regions 87 of the internal prosthesis engagement member lumens 86a, 86b, whereby, as shown in FIG. 6, the prosthesis module 100a can be threadably engaged to the first or second elongated partially cylindrical section 76a, 76b of the multi-function SI joint prosthesis 70b.

In a preferred embodiment, the proximal end 101a of the prosthesis module 100a comprises an internal insertion tool engagement region 110 that is sized and configured to receive and cooperate with an external deployment and/or extraction tool or assembly.

As illustrated in FIG. 3B, in some embodiments, the internal insertion tool engagement region 110 comprises a hex configuration or region that is adapted to receive and cooperate with an external "hex" (or Allen head) deployment and/or extraction tool or assembly.

In some embodiments, the prosthesis module 100a comprises at least one distinguishable surface marking, symbol, line and/or structural pattern and arrangement, which preferably is readily detectable and, hence, readable via a conventional image capture apparatus, such as a fluoroscope and radiography system.

Referring now to FIG. 3C, there is shown another embodiment of a prosthesis module of the invention.

As illustrated in FIG. 3C, the prosthesis module 100b comprises a fenestrated member similarly comprising proximal and distal ends 101a, 101b, a head region 102b disposed proximate the proximal end 101a, and a threaded end region 104 disposed proximate the distal end 101b.

In a preferred embodiment, the head region 102b of the prosthesis module 100b comprises an internal region that is adapted to receive an osteogenic and/or pharmacological agent composition of the invention.

As further illustrated in FIG. 3C, the head region 102b of the prosthesis module 100b further comprises a plurality of apertures 108 that are preferably in communication with the internal region of the prosthesis module 101b and, hence, osteogenic and/or pharmacological agent composition contained therein. According to the invention, the apertures 108 are sized and configured to allow the osteogenic and/or pharmacological agent composition to be dispersed out and delivered to a dysfunctional SI joint and/or structure proximate thereto when the prosthesis module 101b, and, hence, multi-function SI joint prosthesis 70b is disposed in the dysfunctional SI joint.

As illustrated in FIGS. 7 and 8, in a preferred embodiment, the prosthesis module 100b is similarly sized and configured to engage and be translated into the internal prosthesis engagement member lumens 86a, 86b of the first and second elongated partially cylindrical sections 76a, 76b.

As further illustrated in FIG. 3C, in a preferred embodiment of the invention, the threaded end region 104 of the prosthesis module 100b similarly comprises at least one thread 106 that is sized and configured to cooperate with the internal threaded regions 87 of the internal prosthesis engagement member lumens 86a, 86b, whereby, as shown in FIG. 8, the prosthesis module 100b can similarly be threadably engaged to the first or second elongated partially cylindrical section 76a, 76b of the multi-function SI joint prosthesis 70b.

In a preferred embodiment, the proximal end 101a of the prosthesis module 100b similarly comprises an internal insertion tool engagement region 110, such as hex configuration or region that is illustrated in FIG. 3B, which is sized and configured to receive and cooperate with an external deployment and/or extraction tool or assembly.

According to the invention, the prosthesis module 100b can similarly further comprise at least one distinguishable surface marking, symbol, line and/or structural pattern and arrangement, which preferably is readily detectable and, hence, readable via a conventional image capture apparatus, such as a fluoroscope and radiography system.

Referring now to FIG. 3D, there is shown another embodiment of a prosthesis module of the invention, which, according to the invention, can comprise a biodegradable (or bioabsorbable) member comprising an osteogenic and/or pharmacological agent composition.

As illustrated in FIG. 3D, the prosthesis module 100c similarly comprises proximal and distal ends 101a, 101b, a head region 102c disposed proximate the proximal end 101a, and a threaded end region 104 disposed proximate the distal end 101b.

As illustrated in FIGS. 9 and 10, in a preferred embodiment, the prosthesis module 100c is similarly sized and configured to engage and be translated into the internal prosthesis engagement member lumens 86a, 86b of the first and second elongated partially cylindrical sections 76a, 76b, as described above.

In a preferred embodiment, the prosthesis module 100c is similarly configured, whereby, when the prosthesis module 100c is engaged to the multi-function SI joint prosthesis 70b, as described above, the threaded end region 104 of the prosthesis module 100c is disposed in the internal prosthesis engagement member lumen 86a of the first elongated partially cylindrical sections 76a, such as illustrated in FIG. 10, or in the internal prosthesis engagement member lumen 86b of the second elongated partially cylindrical section 76b.

As further illustrated in FIG. 3D, in a preferred embodiment of the invention, the threaded end region 104 of the prosthesis module 100c similarly comprises at least one thread 106 that is sized and configured to cooperate with the internal threaded regions 87 of the internal prosthesis engagement member lumens 86a, 86b, whereby, as shown in FIG. 10, the prosthesis module 100c can similarly be threadably engaged to the first or second elongated partially cylindrical section 76a, 76b of the multi-function SI joint prosthesis 70b.

In a preferred embodiment, the proximal end 101a of the prosthesis module 100c similarly comprises an internal insertion tool engagement region 110, such as hex configuration or region that is illustrated in FIG. 3B, which is sized and configured to receive and cooperate with an external deployment and/or extraction tool or assembly.

According to the invention, the multi-function SI joint prosthesis 70b can comprise any combination of prosthesis modules 100a, 100b, 100c.

By way of example, in some embodiments, the multi-function SI joint prosthesis 70b comprises two (2) prosthesis modules 100a, i.e., prothesis modules comprising sensor apparatus or systems or a first prosthesis module 100a comprising a sensor apparatus or system and a second prosthesis module 100a comprising a neurostimulation apparatus or system, such as illustrated in FIG. 11.

In some embodiments, the multi-function SI joint prosthesis 70b comprises prothesis module 100a, comprising a sensor system or neurostimulation system, and prosthesis module 100b, i.e., a fenestrated module comprising an osteogenic and/or pharmacological agent, such as illustrated in FIG. 12.

In some embodiments, the multi-function SI joint prosthesis 70b comprises prothesis module 100a, comprising a sensor system or neurostimulation system, and prosthesis module 100c, i.e., a bioabsorbable member comprising an osteogenic or pharmacological composition, or a sintered bone graft material, such as illustrated in FIG. 13.

According to the invention, the threaded internal prosthesis engagement member lumens 86a, 86b of the multi-function SI joint prosthesis 70b can also be employed to connect pharmacological agent delivery members to the multi-function SI joint prosthesis 70b, whereby pharmacological agents can be continuously delivered directly to bone structures.

The threaded internal prosthesis engagement member lumens 86a, 86b of the multi-function SI joint prosthesis 70b can also be employed to connect surgical apparatus and systems, such as a catheter system adapted to deliver an osteogenic or pharmacological agent composition to internal prosthesis engagement member lumens 86a, 86b of the multi-function SI joint prosthesis 70b in vivo, to the multi-function SI joint prosthesis 70b.

As set forth in Co-pending U.S. application Ser. No. 17/899,926, the threaded internal prosthesis engagement member lumens 86a, 86b of the multi-function SI joint prosthesis 70b are also sized and configured to engage spine stabilization engagement means of a spinopelvic stabilization system.

As will readily be appreciated by one having ordinary skill in the art, the present invention provides numerous advantages compared to prior art systems and methods for stabilizing dysfunctional SI joints. Among the advantages are the following:

the provision of improved minimally-invasive SI joint stabilization systems and apparatus, and methods of using same, which facilitate posterior trajectory placement of bone structure prostheses in dysfunctional SI joints and, thereby, stabilization of the dysfunctional SI joints;

the provision of improved minimally-invasive SI joint stabilization systems and apparatus, including improved bone structure prostheses, which, when employed to stabilize dysfunctional SI joints, disrupt less tissue and muscles, and avoid nerves and large blood vessels;

the provision of improved minimally-invasive SI joint stabilization systems and apparatus, including improved bone structure prostheses, which can be readily employed to stabilize dysfunctional SI joints the provision of improved minimally-invasive SI joint stabilization systems and apparatus, including improved bone structure prostheses, which, when employed to stabilize dysfunctional SI joints, effectively ameliorate pain associated with SI joint dysfunction;

the provision of multi-function bone structure prostheses that can readily be employed in minimally-invasive SI joint stabilization methods;

the provision of multi-function bone structure prostheses that facilitate remodeling of damaged osseous tissue and regeneration of new osseous tissue and osseous tissue structures;

the provision of multi-function bone structure prostheses that are adapted to provide neurostimulation of anatomical structures associated with SI joints when implanted therein;

the provision of multi-function bone structure prostheses that are adapted to deliver biologically active agents and pharmacological agents to bone structures when implanted therein;

the provision of multi-function bone structure prostheses that are adapted to monitor structural parameters of bone structures when implanted therein; and the provision of multi-function bone structure prostheses that are adapted to monitor physiological and biomechanical parameters associated with bone structures when implanted therein.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A multi-function bone structure prosthesis, comprising:

a monolithic member comprising a first elongated section, a second elongated section and a bridge section, said bridge section disposed between and not extending beyond said first elongated section and said second elongated section in any direction, said bridge section comprising a bridge proximal end and a bridge distal end, said bridge distal end comprising a first tapered region configured and adapted to disrupt at least articular cartilage and cortical bone, said first elongated section comprising a first open proximal end and a first closed distal end, said first elongated section further comprising a second tapered region on said first closed distal end and a first elongate lumen that extends from said first open proximal end to said first closed distal end, said first elongate lumen comprising first internal threads extending from said first open proximal end, said second elongated section comprising a second open proximal end and a second closed distal end, said second elongated section further comprising a third tapered region on said second closed distal end and a second elongate lumen that extends from said second open proximal end to said second closed distal end, said second elongate lumen comprising second internal threads extending from said second open proximal end, said monolithic member further comprising a first prosthesis module, said first prosthesis module adapted to threadably engage at least said first internal threads of said first elongated section and said second internal threads of said second elongated section, said first prosthesis module comprising a neurostimulation system adapted to attenuate pain proximate a dysfunctional SI joint when said monolithic member is advanced therein.

2. The prosthesis of claim 1, wherein said monolithic member is configured and adapted to be advanced into said dysfunctional SI joint via a posterior trajectory.

3. The prosthesis of claim 1, wherein said monolithic member further comprises a second prosthesis module adapted to threadably engage said first internal threads of said first elongated section and said second internal threads of said second elongated section.

4. The prosthesis of claim 3, wherein said second prosthesis module is adapted to monitor at least one physiological parameter associated with said dysfunctional SI joint.

5. The prosthesis of claim 4, wherein said at least one physiological parameter is selected from the group consisting of temperature proximate said dysfunctional SI joint, electrical activity of at least one muscle proximate said dysfunctional SI joint, and contractile capacity of said at least one muscle proximate said dysfunctional SI joint.

6. The prosthesis of claim 3, wherein said second prosthesis module is adapted to monitor at least one biokinetic parameter associated with said dysfunctional SI joint.

7. The prosthesis of claim 6, wherein said at least one biokinetic parameter is selected from the group consisting of motion of said dysfunctional SI joint and force exerted proximate said monolithic member and, thereby, said dysfunctional SI joint.

8. The prosthesis of claim 1, wherein at least said first elongate lumen of said first elongated section is adapted to further receive an osteogenic composition therein.

9. The prosthesis of claim 8, wherein at least said first elongated section of said monolithic member further comprises a plurality of slots in communication with said first elongate lumen, said plurality of slots configured and adapted to allow said osteogenic composition to be dispersed out of said first elongate lumen and delivered to said dysfunctional SI joint when said monolithic member is said advanced into said dysfunctional SI joint.

10. A multi-function bone structure prosthesis, comprising:

a monolithic member adapted to be advanced into a sacroiliac (SI) joint, said monolithic member comprising a first elongated section, a second elongated section and a bridge section, said bridge section disposed between said first elongated section and said second elongated section, said bridge section comprising a bridge proximal end and a bridge distal end, said bridge distal end comprising a first tapered region configured and adapted to disrupt at least articular cartilage and cortical bone, said first elongated section comprising a first open proximal end, a first closed distal end, and a first elongate lumen that extends from said first open proximal end to said first closed distal end, said first elongate lumen comprising first internal threads extending from said first open proximal end, said second elongated section comprising a second open proximal end, a second closed distal end, and a second elongate lumen that extends from said second open proximal end to said second closed distal end, said second elongate lumen comprising second internal threads extending from said second open proximal end, said monolithic member further comprising a first prosthesis module, said first prosthesis module adapted to threadably engage at least said first internal threads of said first elongated section and said second internal threads of said second elongated section, said first prosthesis module comprising a neurostimulation system adapted to attenuate pain proximate said SI joint when said monolithic member is said advanced therein, said monolithic member further comprising a second prosthesis module, said second prosthesis module adapted to threadably engage at least said first internal threads of said first elongated section and said second internal threads of said second elongated section, said second prosthesis module adapted to monitor at least one physiological parameter associated with said SI joint, said at least one physiological parameter selected from the group consisting of temperature proximate said SI joint, electrical activity of at least one muscle proximate said SI joint, and contractile capacity of said at least one muscle proximate said SI joint.

11. The prosthesis of claim 10, wherein said monolithic member is configured and adapted to be said advanced into said SI joint via a posterior trajectory.

12. The prosthesis of claim 10, wherein said second prosthesis module is further adapted to monitor at least one biokinetic parameter associated with said SI joint.

13. The prosthesis of claim 12, wherein said at least one biokinetic parameter is selected from the group consisting of motion of said SI joint and force exerted proximate said monolithic member.

\* \* \* \* \*